United States Patent
Sung et al.

(10) Patent No.: US 12,410,233 B2
(45) Date of Patent: *Sep. 9, 2025

(54) EXTRACELLULAR DOMAIN OF ALPHA SUBUNIT OF IgE Fc RECEPTOR, PHARMACEUTICAL COMPOSITION COMPRISING SAME AND METHOD FOR PRODUCING SAME

(71) Applicant: GI INNOVATION, INC., Seoul (KR)

(72) Inventors: Young Chul Sung, Seoul (KR); Zungyoon Yang, Incheon (KR); Myung Ho Jang, Seoul (KR)

(73) Assignee: GI Innovation, Inc., Seoul (KR)

(*) Notice: Subject to any disclaimer, the term of this patent is extended or adjusted under 35 U.S.C. 154(b) by 176 days.

This patent is subject to a terminal disclaimer.

(21) Appl. No.: 16/958,861

(22) PCT Filed: Jan. 8, 2019

(86) PCT No.: PCT/KR2019/000274
§ 371 (c)(1),
(2) Date: Jun. 29, 2020

(87) PCT Pub. No.: WO2019/135668
PCT Pub. Date: Jul. 11, 2019

(65) Prior Publication Data
US 2021/0070833 A1    Mar. 11, 2021

(30) Foreign Application Priority Data
Jan. 8, 2018  (KR) .................. 10-2018-0002248

(51) Int. Cl.
A23L 33/18    (2016.01)
A61K 38/00    (2006.01)
A61P 37/08    (2006.01)
C07K 14/735   (2006.01)

(52) U.S. Cl.
CPC ........ C07K 14/70535 (2013.01); A23L 33/18 (2016.08); A61P 37/08 (2018.01); A61K 38/00 (2013.01)

(58) Field of Classification Search
CPC .......... C07K 14/70535; C07K 2319/00; A23L 33/18; A61P 37/08; A61K 38/00; A23V 2200/304
See application file for complete search history.

(56) References Cited

U.S. PATENT DOCUMENTS

| | | | |
|---|---|---|---|
| 12,128,076 B2 * | 10/2024 | Jang .................. | A61K 38/1774 |
| 2008/0300188 A1 | 12/2008 | Yang et al. | |
| 2011/0183363 A1 * | 7/2011 | Fischer ............... | G01N 33/564 |
| | | | 530/387.2 |
| 2011/0256641 A1 * | 10/2011 | Ling et al. ......... | G01N 33/6854 |
| | | | 436/513 |
| 2012/0276096 A1 | 11/2012 | Yang et al. | |
| 2018/0193452 A1 * | 7/2018 | Ma ..................... | C07K 16/2878 |

FOREIGN PATENT DOCUMENTS

| | | | | |
|---|---|---|---|---|
| CN | 101611052 A | 12/2009 | | |
| CN | 105175553 A | 12/2015 | | |
| JP | 2007-528194 A | 10/2007 | | |
| JP | 2009-504569 A | 2/2009 | | |
| KR | 10-2017-0120579 A | 10/2017 | | |
| RU | 2500686 C2 | 12/2013 | | |
| TW | 201636373 A | 10/2016 | | |
| TW | 201930343 A | 8/2019 | | |
| WO | 2005/017148 A1 | 2/2005 | | |
| WO | 2007/005786 A2 | 1/2007 | | |
| WO | WO-2008028068 A2 * | 3/2008 | ....... | C07K 14/70535 |
| WO | 2008116149 A2 | 9/2008 | | |
| WO | WO-2008147143 A2 * | 12/2008 | ................ | A61P 1/00 |
| WO | 2009/080816 A1 | 7/2009 | | |
| WO | 2016/108654 A1 | 7/2016 | | |
| WO | 2016/133197 A1 | 8/2016 | | |
| WO | WO-2016200219 A1 * | 12/2016 | ............. | A61K 38/00 |
| WO | 2019/135666 A1 | 7/2019 | | |

OTHER PUBLICATIONS

Putnam et al., Amino Acid Sequence of the First Constant Region Domain and the Hinge Region of the [delta] Heavy Chain of Human IgD, Oct. 1981, Proc. Natl. Acad. Sci. USA, vol. 78 No. 10, pp. 6168-6172 (Year: 1981).*
Schwarzbaum et al., Mapping of murine IgE epitopes involved in IgE-Fc[epsilon] receptor interactions, 1989, Eur. J. Immunol., vol. 19, pp. 1015-1023 (Year: 1989).*
Takahashi et al., The High Affinity IgE Receptor (FceRI) as a Target for Anti-allergic Agents, 2005, Allergology International, vol. 54 No. 1, pp. 1-5 (Year: 2005).*
Rogers et al., Molecular Characterization of Immunoglobulin D in Mammals: Immunoglobulin Heavy Constant Delta Genes in Dogs, Chimpanzees, and Four Old World Monkey Species, 2006, Immunology, vol. 118, pp. 88-100 (Year: 2006).*

(Continued)

*Primary Examiner* — Vanessa L. Ford
*Assistant Examiner* — Danaya L Middleton
(74) *Attorney, Agent, or Firm* — Sughrue Mion, PLLC

(57) ABSTRACT

The present invention provides a polypeptide dimeric protein containing two monomers, each of which contains an extracellular domain (FcεRIa-ECD) of an alpha subunit of an IgE Fc receptor. The dimeric protein according to the present invention has advantages that an excellent binding ability to IgE is exhibited as compared with a conventional therapeutic agent containing an anti-IgE antibody, and less other side effects are exhibited due to lack of ADCC and CDC functions. Thus, the dimeric protein can be applied to a medical product for treating or preventing an IgE-mediated allergic disease.

12 Claims, 13 Drawing Sheets

Specification includes a Sequence Listing.

(56) References Cited

OTHER PUBLICATIONS

Byrne et al., Sialic Acids: Carbohydrate Moieties That Influence The Biological and Physical Properties of Biopharmaceutical Proteins and Living Cells, Apr. 2007, Drug Discovery Today, vol. 12 Nos. 7/8, pp. 319-326 (Year: 2007).*

Saban et al., "Human FcERI-IgG and humanized anti-IgE monoclonal antibody MaE11 block passive sensitization of human and rhesus monkey lung", Journal of Allergy and Clinical Immunology, 1994, vol. 94, No. 5, pp. 836-843 (8 pages total).

Haak-Frendscho et al., "Human IgE Receptor α-Chain IgG Chimera Blocks Passive Cutaneous Anaphylaxis Reaction In Vivo", The Journal of Immunology, 1993, vol. 151, pp. 351-358 (8 pages total).

Zoller et al., "Oligonucleotide-directed mutagenesis using M13-derived vectors: an efficient and general procedure for the production of point mutations in any fragment of DNA", Nucleic Acids Research, vol. 10, No. 20, 1982, p. 6487-6500 (14 pages).

S.C. Garman, et al., "Chain A, High Affinity Immunoglobulin Epsilon Receptor Alpha-Subunit", NCBI, Genbank Acession No. 1J89A, Oct. 10, 2012, 4 pages.

A.L. Flamar, et al., "Anti-human CD40 12E12 antibody HIV antigen fusion protein [synthetic construct]", NCBI, Genbank Acession No. AJD85779.1, Jan. 19, 2015, 3 pages.

M.B. White, et al., "immunoglobulin delta-chain, partial [*Home sapiens*]", NCBI, Genbank Acession No. AAA52771.1, Aug. 1, 2016, 3 pages.

M.B. White, et al., "immunoglobulin delta-chain, partial [*Home sapiens*]", NCBI, Genbank Acession No. AAA52770.1, Aug. 1, 2016, 3 pages.

Kyoko Takahashi, et al., "The High Affinity IgE Receptor (FcεRI) as a Target for Anti-allergic Agents", Allergology International, 2005, pp. 1-5, vol. 54, No. 1.

J.C. Venter, et al., "Fc fragment of IgE, high affinity I, receptor for; alpha polypeptide [*Homo sapiens*]", NCBI GenBank EAW52789.1, Mar. 23, 2015, 2 pages.

International Search Report for PCT/KR2019/000274 dated Apr. 15, 2019 (PCT/ISA/210).

Communication dated Feb. 18, 2023 issued by the State Intellectual Property Office of the P.R. China in application No. 2019800079175.

\* cited by examiner

[FIG. 1A]
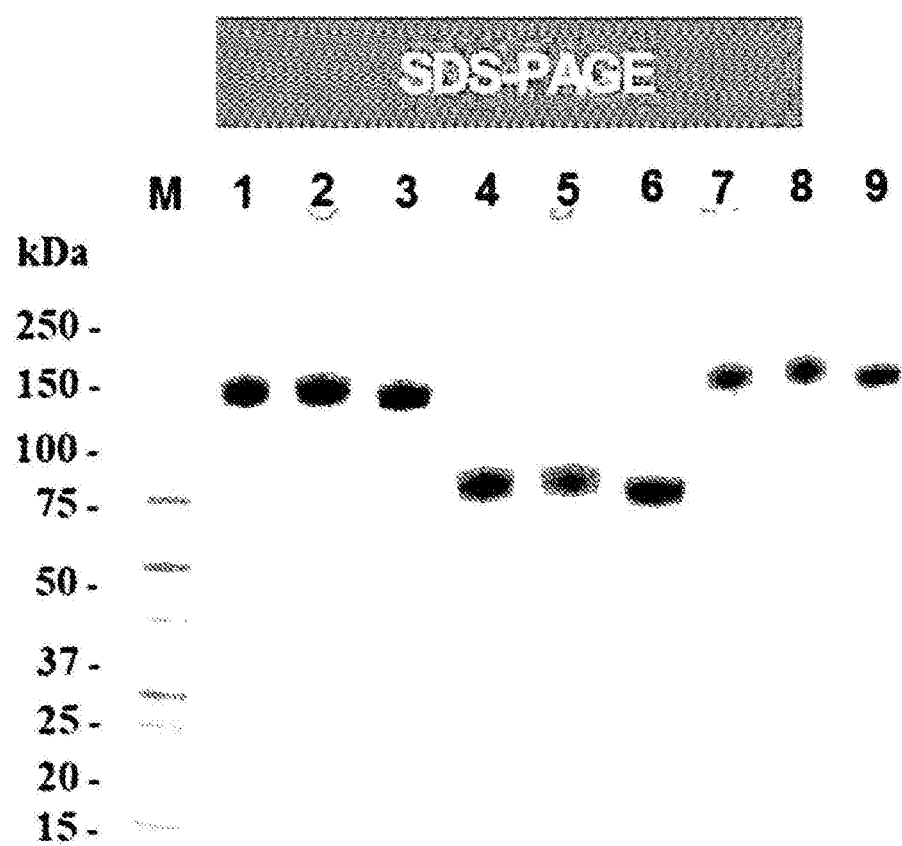

[FIG. 1B]

| Lane # | Sample | Purification | Purity (SE-HPLC) | Sample condition | |
|---|---|---|---|---|---|
| M | Protein standard | One-step (Protein-A column) purification | - | - | - |
| 1 | FcεR1α ECD-Fc3 | | 94.5% | - | Non-reducing |
| 2 | FcεR1α ECD-Fc3+2,6 ST | | 93.7% | | |
| 3 | FcεR1α ECD-Fc2+2,6 ST | | 93.2% | | |
| 4 | FcεR1α ECD-Fc3 | | 94.5% | - | Reducing |
| 5 | FcεR1α ECD-Fc3+2,6 ST | | 93.7% | | |
| 6 | FcεR1α ECD-Fc2+2,6 ST | | 93.2% | | |
| 7 | FcεR1α ECD-Fc3 | | 94.5% | Freezing/Thawing test | Non-reducing |
| 8 | FcεR1α ECD-Fc3+2,6 ST | | 93.7% | | |
| 9 | FcεR1α ECD-Fc3+2,6 ST | | 93.2% | | |

[FIG. 1C]
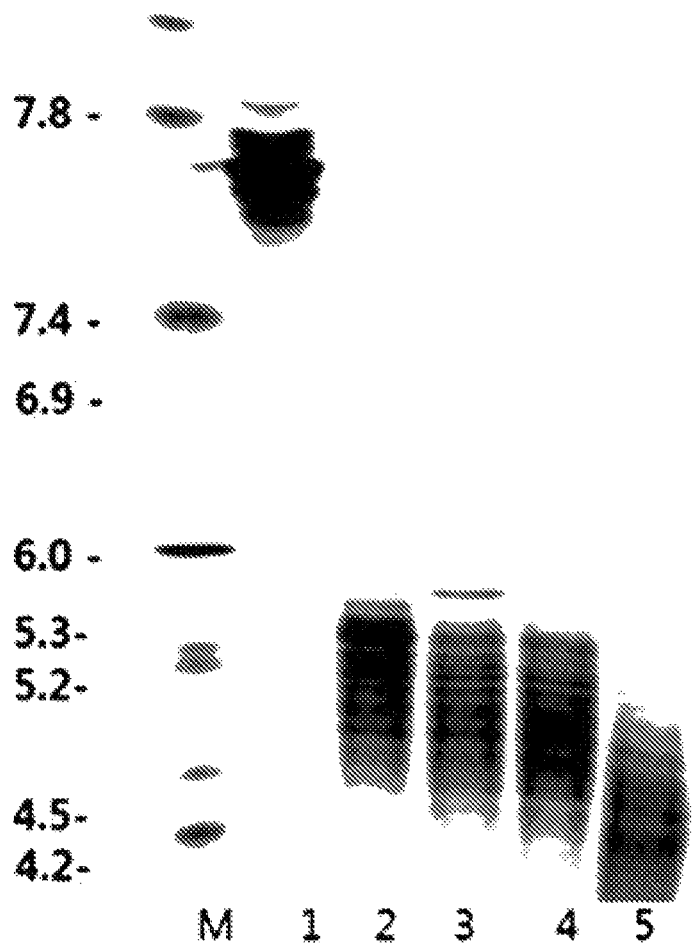
| Lane | Loading sample | Theoretical pI |
|---|---|---|
| M | Marker (SERVA pH3-10, 5uL) | |
| 1 | Xolair | 7.03 |
| 2 | FcεRIα ECD-FC2 | 5.62 |
| 3 | FcεRIα ECD-FC2+2,6 ST | 5.62 |
| 4 | FcεRIα ECD-FC3 | 5.63 |
| 5 | FcεRIα ECD-FC3+2,6 ST | 5.63 |

[FIG. 2]
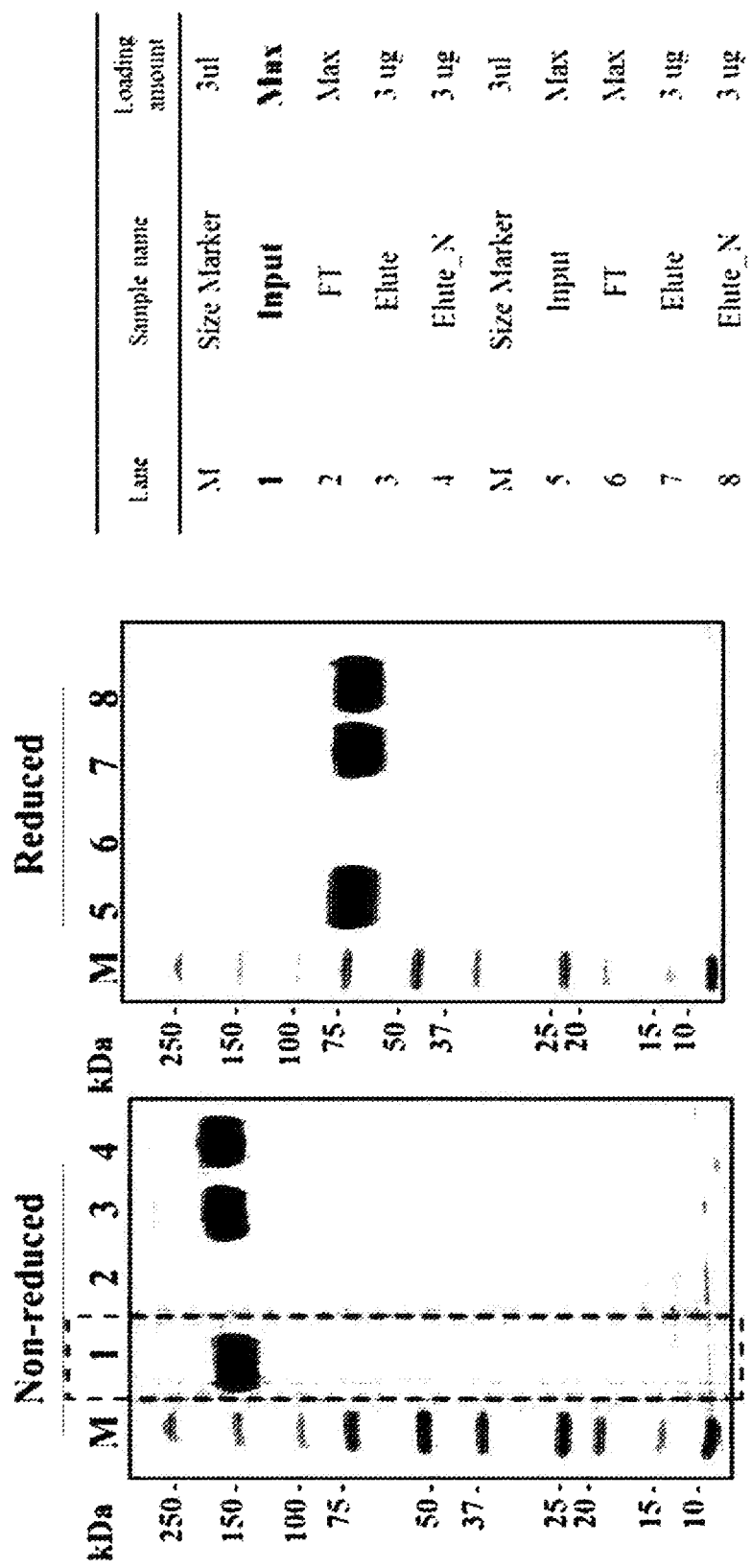

[FIG. 3]
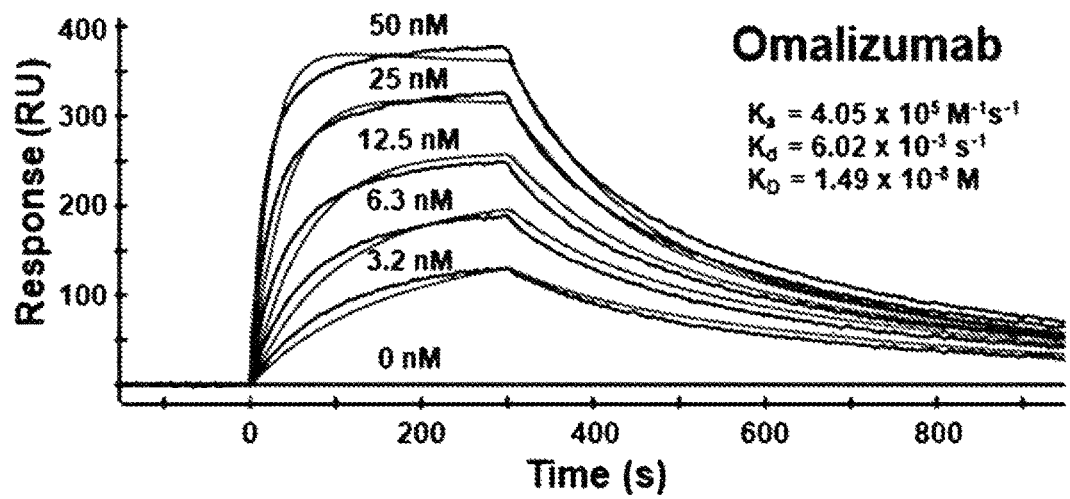
[FIG. 4]
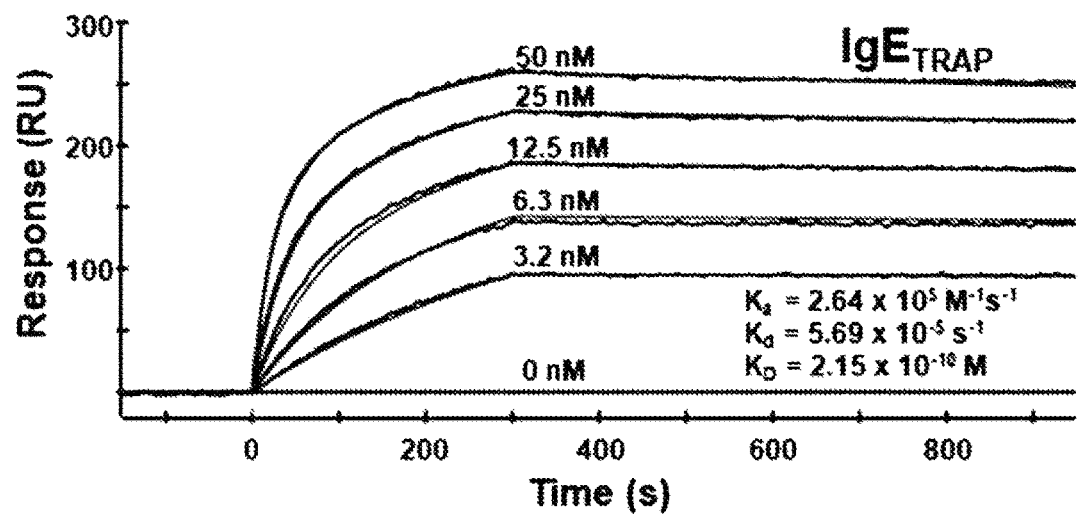

[FIG. 5A]
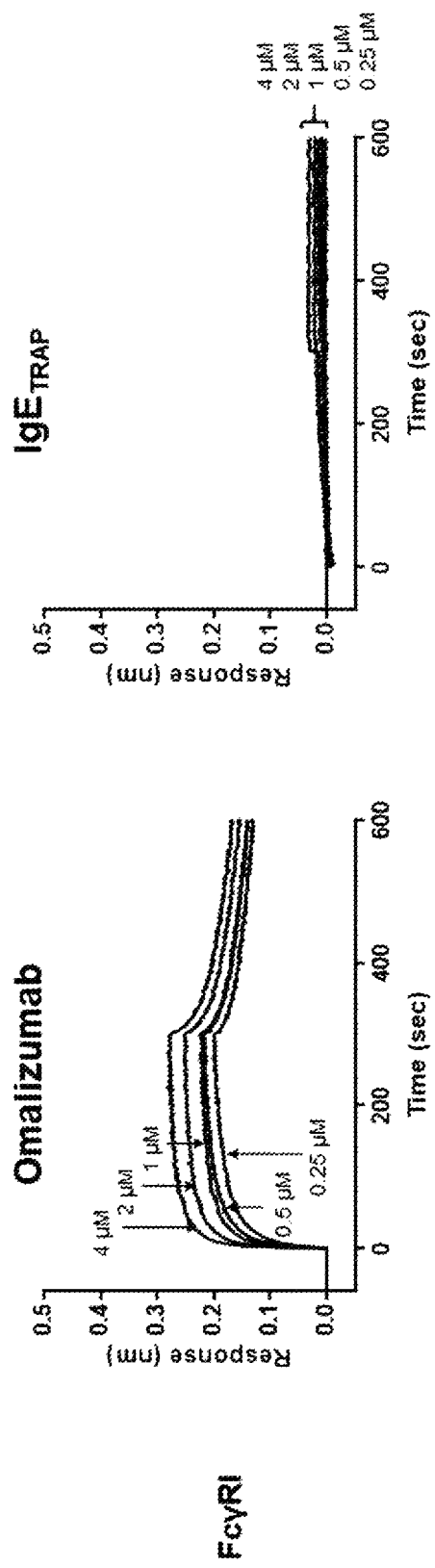

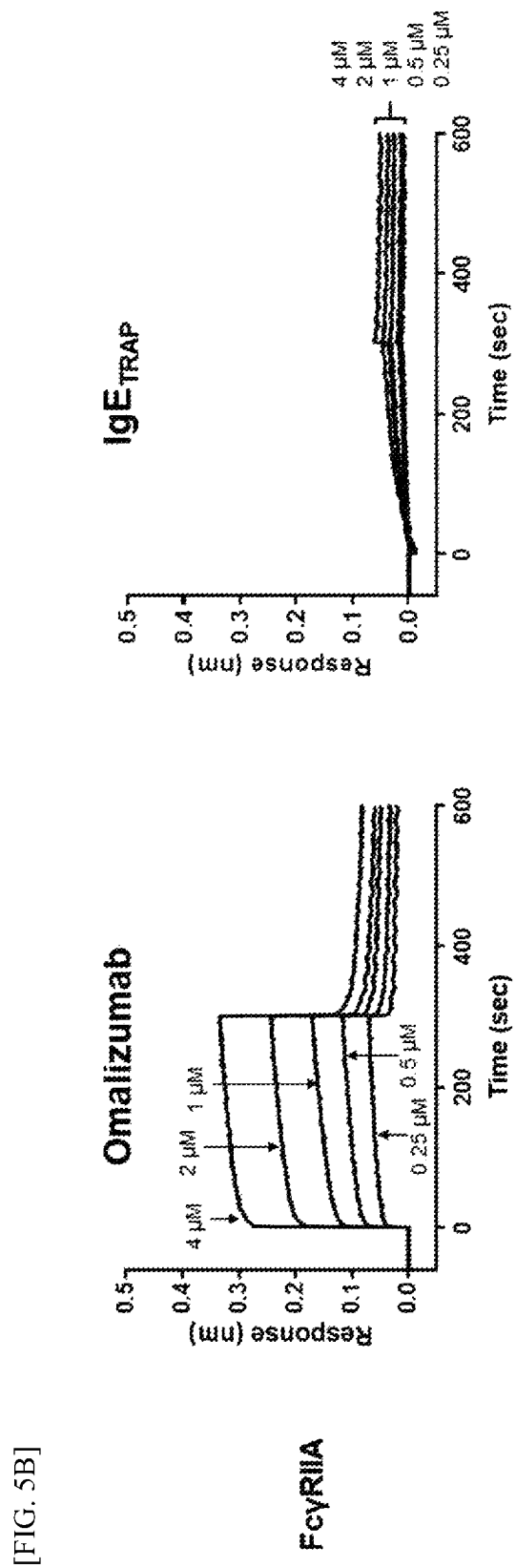
[FIG. 5B]

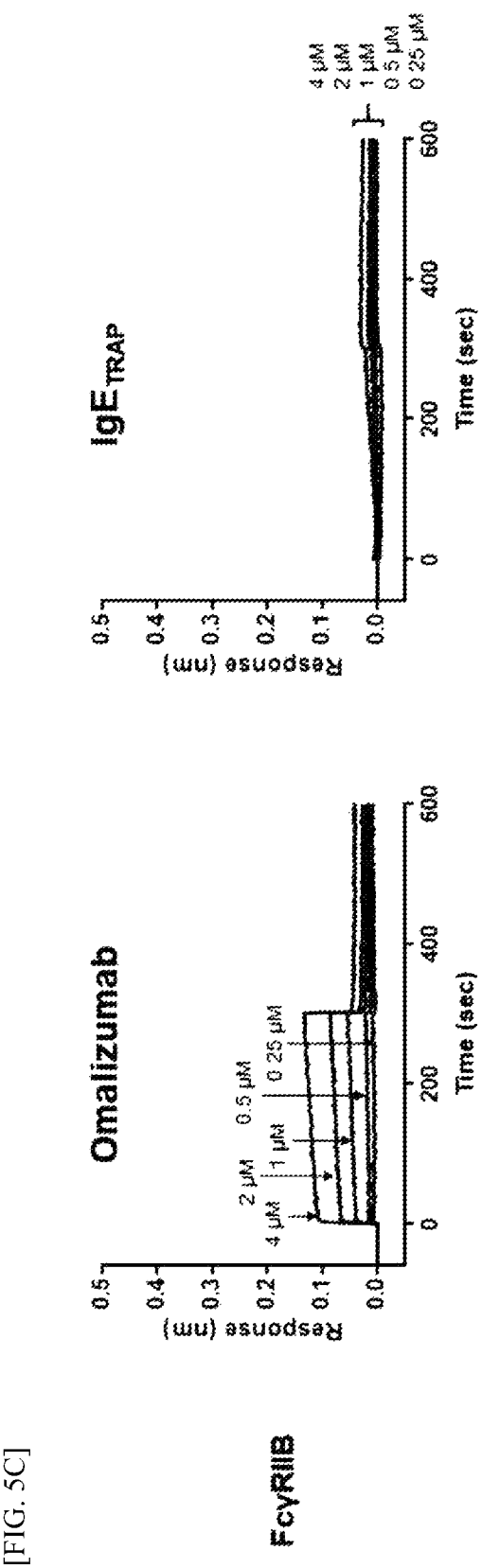
[FIG. 5C]

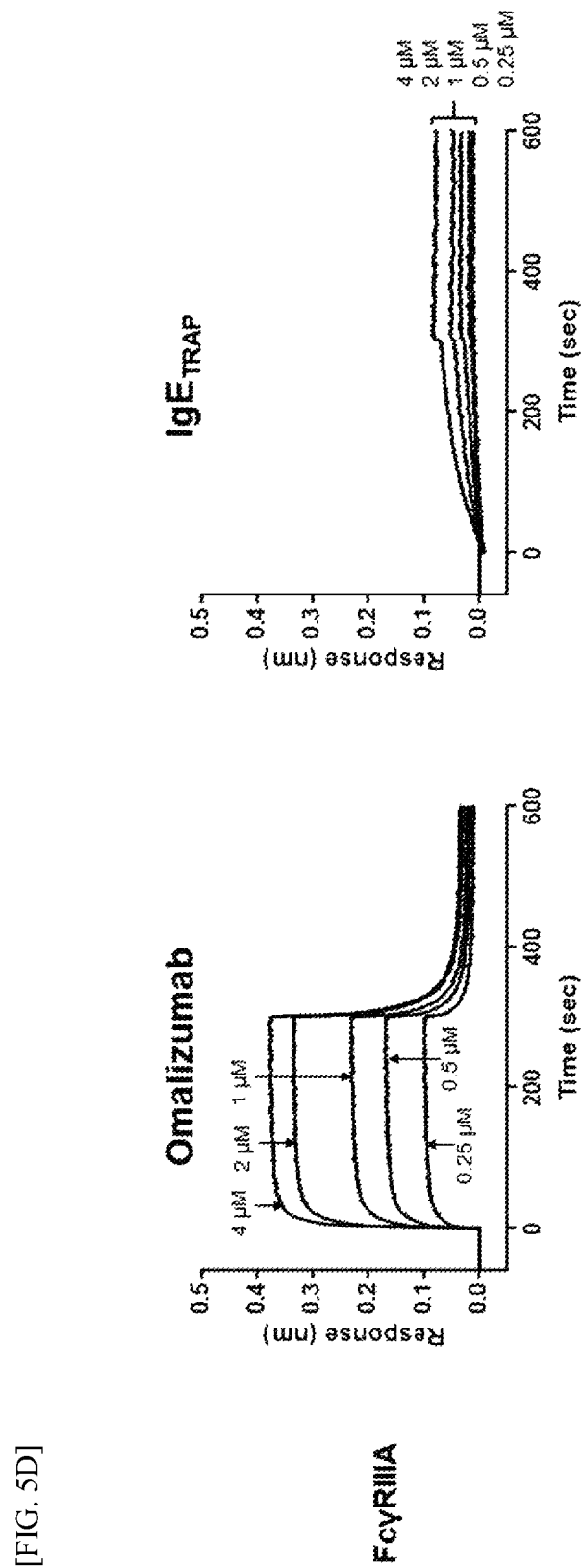
[FIG. 5D]

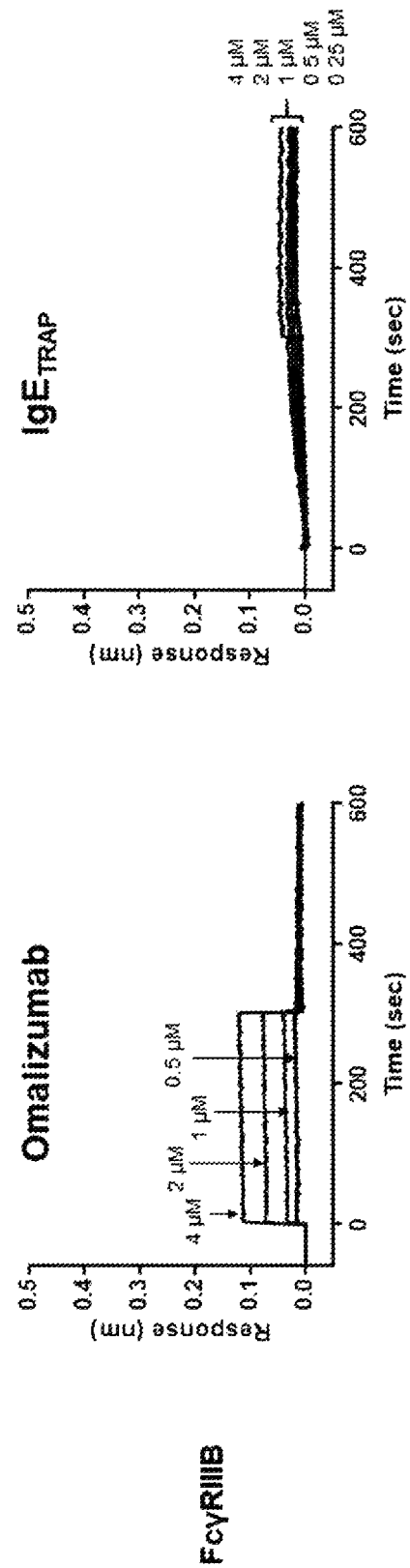
[FIG. 5E]

[FIG. 6]
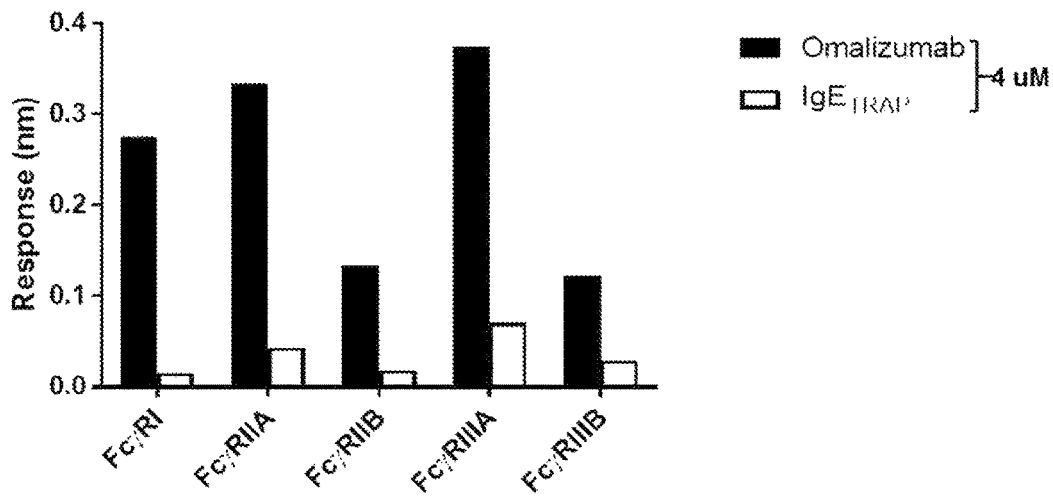
[FIG. 7]
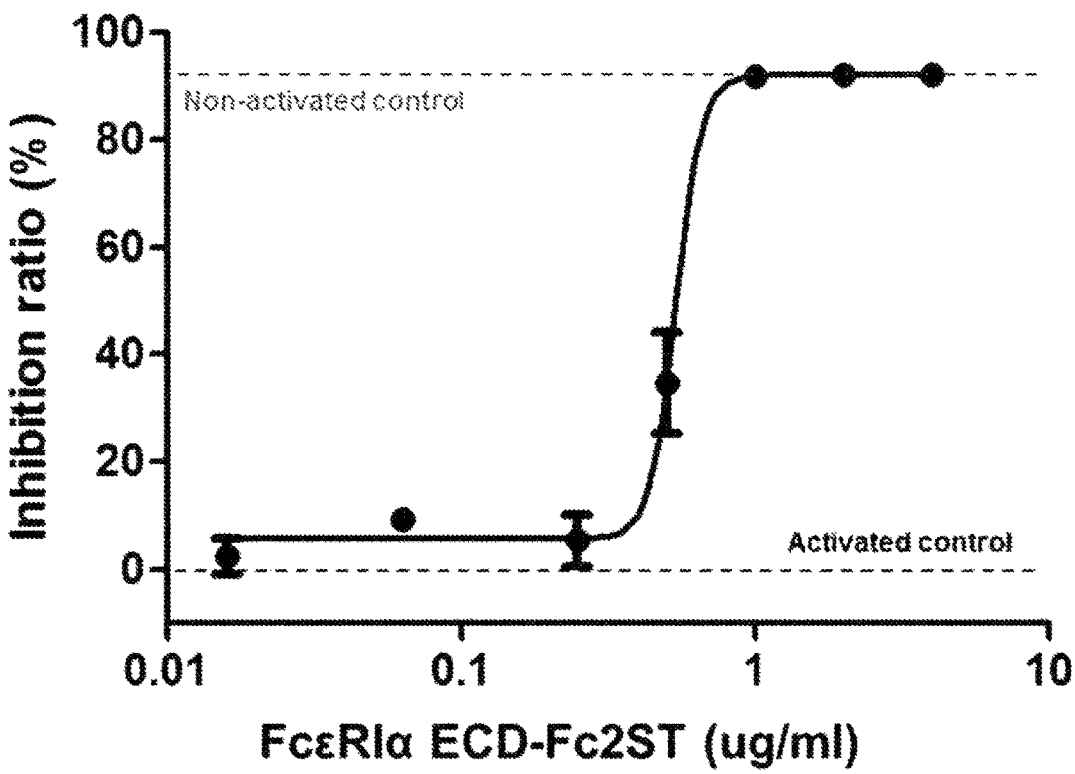

[FIG. 8]
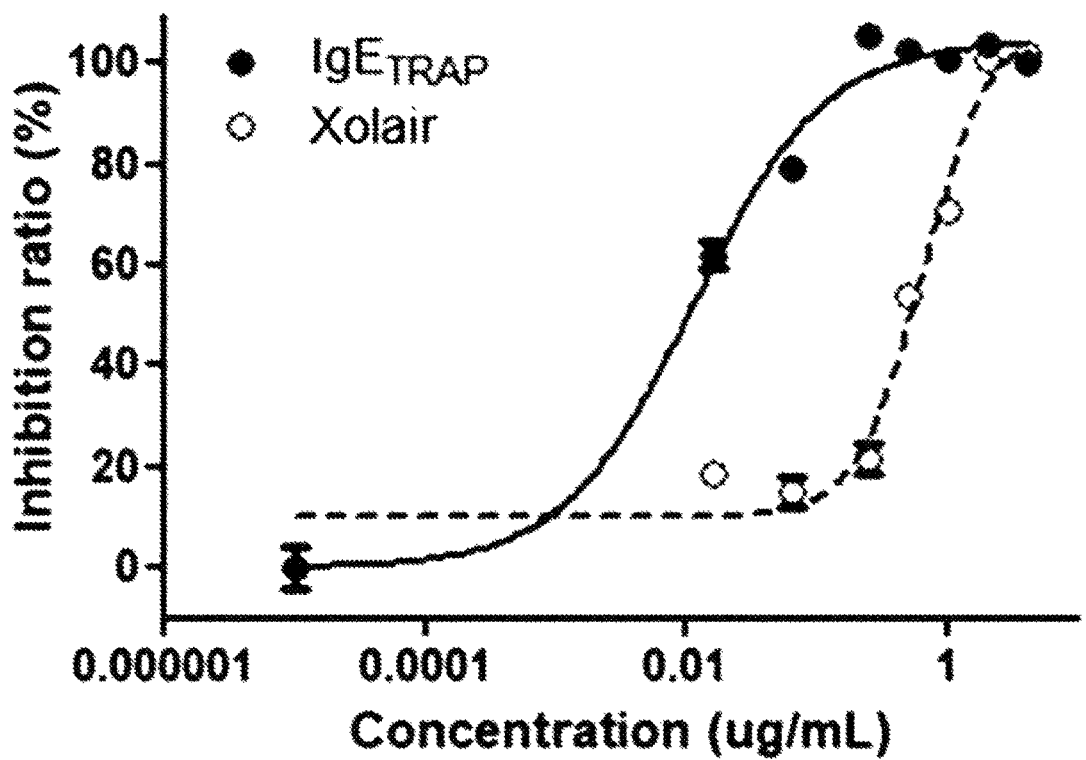

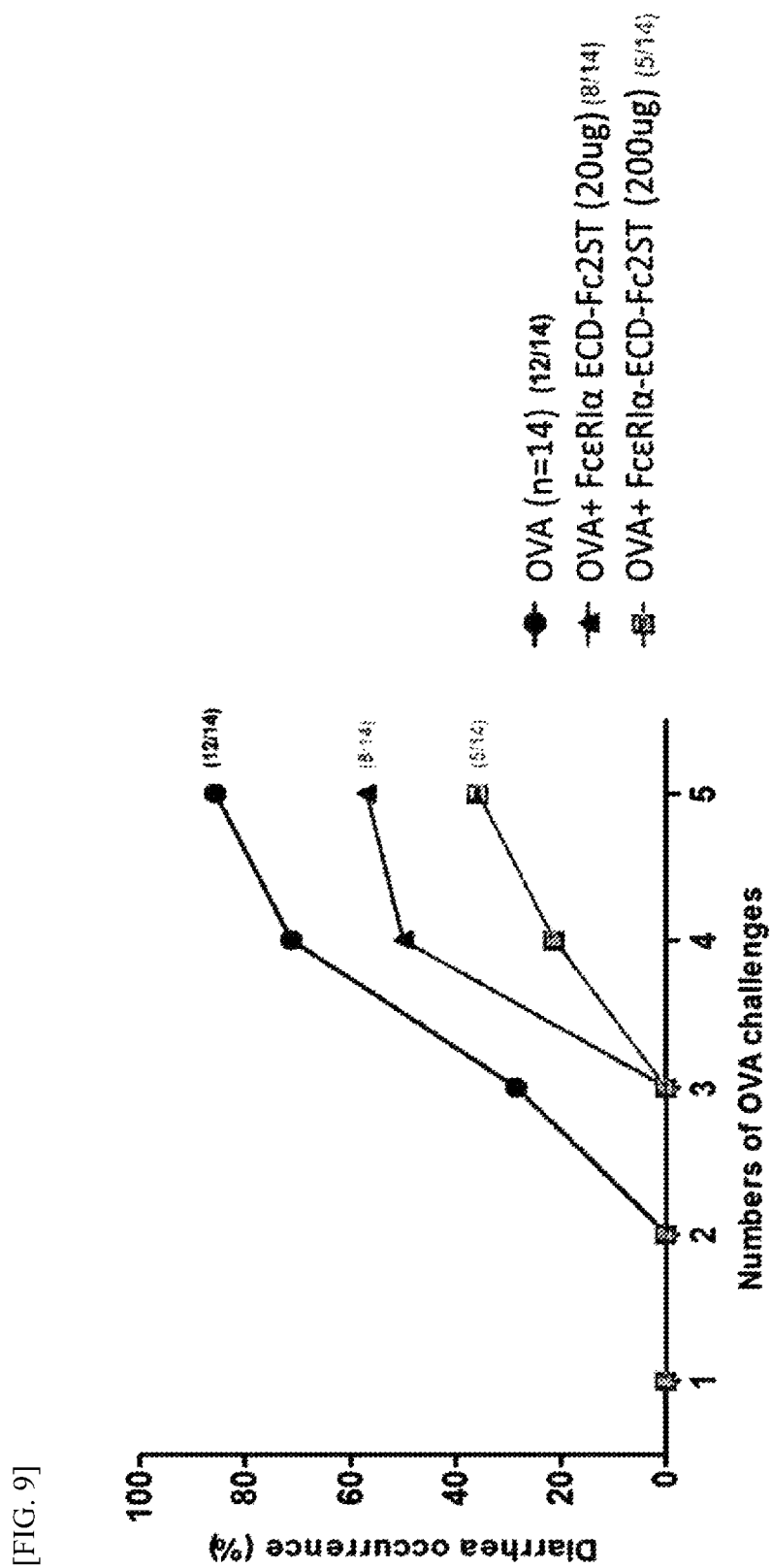
[FIG. 9]

SEQUENCE LISTING

```
<160> NUMBER OF SEQ ID NOS: 22

<210> SEQ ID NO 1
<211> LENGTH: 180
<212> TYPE: PRT
<213> ORGANISM: Artificial Sequence
<220> FEATURE:
<223> OTHER INFORMATION: FCeRI1 ECD

<400> SEQUENCE: 1

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln
```

```
<210> SEQ ID NO 2
<211> LENGTH: 215
<212> TYPE: PRT
<213> ORGANISM: Artificial Sequence
<220> FEATURE:
<223> OTHER INFORMATION: Modified Fc

<400> SEQUENCE: 2

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Met Thr Lys
        115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215

<210> SEQ ID NO 3
<211> LENGTH: 30
<212> TYPE: PRT
<213> ORGANISM: Artificial Sequence
<220> FEATURE:
<223> OTHER INFORMATION: IgD hinge variant

<400> SEQUENCE: 3

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro
            20                  25                  30

<210> SEQ ID NO 4
<211> LENGTH: 49
<212> TYPE: PRT
<213> ORGANISM: Artificial Sequence
<220> FEATURE:
<223> OTHER INFORMATION: IgD hinge variant

<400> SEQUENCE: 4
```

```
Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Lys Lys Gly Ser
            20                  25                  30

Lys Glu Lys Glu Glu Gln Glu Glu Arg Glu Thr Lys Thr Pro Glu Cys
        35                  40                  45

Pro

<210> SEQ ID NO 5
<211> LENGTH: 540
<212> TYPE: DNA
<213> ORGANISM: Artificial Sequence
<220> FEATURE:
<223> OTHER INFORMATION: nucleotides sequence of FCeRI1 ECD

<400> SEQUENCE: 5
gtgccccaga agcccaaggt gagcctgaac cctccctgga acagaatctt caagggcgag    60
aacgtgaccc tgacctgcaa cggcaacaac ttcttcgagg tgagcagcac caagtggttc   120
cacaatggca gcctgagcga ggagaccaac agctccctga catcgtgaa cgccaagttc   180 gaggacagcg gcgagtacaa gtgccagcac cagcaggtga cgagagcga gcccgtgtac   240 ctggaggtgt tcagcgactg gctgctgctg caggccagcg ccgaggtggt gatggagggc   300
cagcccctgt tcctgagatg ccacggctgg agaaactggg acgtgtacaa ggtgatctac   360
tacaaggatg gcgaggccct gaagtactgg tacgagaacc acaacatctc catcaccaac   420
gccaccgtgg aggacagcgg cacctactac tgcacaggca aggtgtggca gctggactac   480
gagagcgagc ccctgaacat caccgtgatc aaggctccca gagagaagta ctggctgcag   540

<210> SEQ ID NO 6
<211> LENGTH: 561
<212> TYPE: DNA
<213> ORGANISM: Artificial Sequence
<220> FEATURE:
<223> OTHER INFORMATION: nucleotides sequence of modified Fc

<400> SEQUENCE: 6
tgcgtggtcg tggatgtgag ccaggaagat cccgaagtgc agttcaactg gtacgtggat    60
ggcgtggaag tgcacaacgc caagaccaag cccagagaag agcagttcaa ctccacctac   120
agagtggtga gcgtgctgac cgtgctgcac caggactggc tgaacggcaa ggagtacaag   180
tgcaaggtgt ccaacaaagg cctgcccagc tccatcgaga gaccatcag caaagccaaa   240 ggccagccca gagaacccca ggtgtacacc ctgcctccca gcaggaaga gatgaccaag   300 aaccaggtgt ccctgacctg cctggtgaaa ggcttctacc ccagcgacat cgccgtggag   360
tgggaaagca acggccagcc cgagaacaat tacaagacaa cccctcccgt gctggatagc   420
gatggcagct ctttctgta cagcagactg accgtggaca agagcagatg gcaggaaggc   480
aacgtgttca gctgcagcgt gatgcacgaa gccctgcaca ccactacac ccagaagagc   540 ctgtccctga gcctgggcaa g                                              561

<210> SEQ ID NO 7
<211> LENGTH: 174
<212> TYPE: DNA
<213> ORGANISM: Artificial Sequence
<220> FEATURE:
<223> OTHER INFORMATION: nucleotides sequence of IgD hinge variant

<400> SEQUENCE: 7
```

```
aggaacaccg gcagaggagg cgaggaaaag aaaggaagca aggagaagga ggagcaggag      60
gaaagagaaa ccaagacccc cgagtgcccc agccacaccc agcccctggg cgtgttcctg     120
ttccccccca agcccaagga caccctgatg atcagcagaa ccccgaggt gacc            174
```

<210> SEQ ID NO 8
<211> LENGTH: 231
<212> TYPE: DNA
<213> ORGANISM: Artificial Sequence
<220> FEATURE:
<223> OTHER INFORMATION: nucleotides sequence of IgD hinge variant

<400> SEQUENCE: 8

```
gcccagcccc aggccgaggg cagcctggct aaggccacca cagctcccgc caccaccagg      60
aacaccggca gaggaggcga ggaaaagaaa ggaagcaagg agaaggagga gcaggaggaa     120
agagaaacca gaccccccga gtgccccagc cacacccagc cctgggcgt gttcctgttc     180 ccccccaagc ccaaggacac cctgatgatc agcagaaccc cgaggtgac c               231
```

<210> SEQ ID NO 9
<211> LENGTH: 25
<212> TYPE: PRT
<213> ORGANISM: Artificial Sequence
<220> FEATURE:
<223> OTHER INFORMATION: signal peptide

<400> SEQUENCE: 9

```
Met Asp Ala Met Leu Arg Gly Leu Cys Cys Val Leu Leu Leu Cys Gly
1               5                   10                  15

Ala Val Phe Val Ser Pro Ser His Ala
            20                  25
```

<210> SEQ ID NO 10
<211> LENGTH: 75
<212> TYPE: DNA
<213> ORGANISM: Artificial Sequence
<220> FEATURE:
<223> OTHER INFORMATION: nucleotides sequence of signal peptide

<400> SEQUENCE: 10

```
atggacgcca tgctgagagg cctgtgctgt gtgctgctgc tgtgcggcgc cgtgttcgtg      60
tcccctagcc acgcc                                                      75
```

<210> SEQ ID NO 11
<211> LENGTH: 450
<212> TYPE: PRT
<213> ORGANISM: Artificial Sequence
<220> FEATURE:
<223> OTHER INFORMATION: FceRIa ECD-hinge-Fc2

<400> SEQUENCE: 11

```
Met Asp Ala Met Leu Arg Gly Leu Cys Cys Val Leu Leu Leu Cys Gly
1               5                   10                  15

Ala Val Phe Val Ser Pro Ser His Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80
```

Val Asn Ala Lys Phe Glu Asp Ser Gly Glu Tyr Lys Cys Gln His Gln
            85                  90                  95

Gln Val Asn Glu Ser Glu Pro Val Tyr Leu Glu Val Phe Ser Asp Trp
100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Tyr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Arg Asn Thr
        195                 200                 205

Gly Arg Gly Gly Glu Glu Lys Lys Gly Ser Lys Glu Lys Glu Glu Gln
210                 215                 220

Glu Glu Arg Glu Thr Lys Thr Pro Glu Cys Pro Ser His Thr Gln Pro
225                 230                 235                 240

Leu Gly Val Phe Leu Phe Pro Pro Lys Pro Lys Asp Thr Leu Met Ile
                245                 250                 255

Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 12
<211> LENGTH: 1350
<212> TYPE: DNA
<213> ORGANISM: Artificial Sequence
<220> FEATURE:

<223> OTHER INFORMATION: nucleotides sequence of FceRIa ECD-hinge-Fc2

<400> SEQUENCE: 12

```
atggacgcca tgctgagagg cctgtgctgt gtgctgctgc tgtgcggcgc cgtgttcgtg      60
tcccctagcc acgccgtgcc ccagaagccc aaggtgagcc tgaaccctcc ctggaacaga     120
atcttcaagg gcgagaacgt gaccctgacc tgcaacggca caacttcttc cgaggtgagc     180
agcaccaagt ggttccacaa tggcagcctg agcgaggaga ccaacagctc cctgaacatc     240
gtgaacgcca agttcgagga cagcggcgag tacaagtgcc agcaccagca ggtgaacgag     300
agcgagcccg tgtacctgga ggtgttcagc gactggctgc tgctgcaggc cagcgccgag     360
gtggtgatgg agggccagcc cctgttcctg agatgccacg ctggagaaa ctgggacgtg      420
tacaaggtga tctactacaa ggatggcgag gccctgaagt actggtacga gaaccacaac     480
atctccatca ccaacgccac cgtggaggac agcggcacct actactgcac aggcaaggtg     540
tggcagctgg actacgagag cgagcccctg aacatcaccg tgatcaaggc tcccagagag     600
aagtactggc tgcagaggaa caccggcaga ggaggcgagg aaaagaaagg aagcaaggag     660
aaggaggagc aggaggaaag agaaaccaag accccgagt gccccagcca cccagccc        720
ctgggcgtgt cctgttccc ccccaagccc aaggacaccc tgatgatcag cagaaccccc      780
gaggtgacct gcgtggtcgt ggatgtgagc caggaagatc ccgaagtgca gttcaactgg     840
tacgtggatg gcgtggaagt gcacaacgcc aagaccaagc cagaagaaga gcagttcaac     900
tccacctaca gagtggtgag cgtgctgacc gtgctgcacc aggactggct gaacggcaag     960
gagtacaagt gcaaggtgtc caacaaaggc ctgcccagct ccatcgagaa gaccatcagc    1020
aaagccaaag gccagcccag agaaccccag gtgtacaccc tgcctcccag ccaggaagag    1080
atgaccaaga accaggtgtc cctgacctgc ctggtgaaag cttctaccc cagcgacatc     1140
gccgtggagt gggaaagcaa cggccagccc gagaacaatt acaagacaac ccctcccgtg    1200
ctggatagcg atggcagctt ctttctgtac agcagactga ccgtggacaa gagcagatgg    1260
caggaaggca acgtgttcag ctgcagcgtg atgcacgaag ccctgcacaa ccactacacc    1320
cagaagagcc tgtccctgag cctgggcaag                                     1350
```

<210> SEQ ID NO 13
<211> LENGTH: 469
<212> TYPE: PRT
<213> ORGANISM: Artificial Sequence
<220> FEATURE:
<223> OTHER INFORMATION: FceRIa ECD-hinge-Fc3

<400> SEQUENCE: 13

Met Asp Ala Met Leu Arg Gly Leu Cys Cys Val Leu Leu Cys Gly
1               5                   10                  15

Ala Val Phe Val Ser Pro Ser His Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp

```
            100             105              110
Leu Leu Leu Gln Ala Ser Ala Glu Val Val Met Glu Gly Gln Pro Leu
        115             120             125

Phe Leu Arg Cys His Gly Trp Arg Asn Trp Asp Val Tyr Lys Val Ile
        130             135             140

Tyr Tyr Lys Asp Gly Glu Ala Leu Lys Tyr Trp Tyr Glu Asn His Asn
145             150             155             160

Ile Ser Ile Thr Asn Ala Thr Val Glu Asp Ser Gly Thr Tyr Tyr Cys
            165             170             175

Thr Gly Lys Val Trp Gln Leu Asp Tyr Glu Ser Glu Pro Leu Asn Ile
        180             185             190

Thr Val Ile Lys Ala Pro Arg Glu Lys Tyr Trp Leu Gln Ala Gln Pro
        195             200             205

Gln Ala Glu Gly Ser Leu Ala Lys Ala Thr Thr Ala Pro Ala Thr Thr
        210             215             220

Arg Asn Thr Gly Arg Gly Gly Glu Glu Lys Lys Gly Ser Lys Glu Lys
225             230             235             240

Glu Glu Gln Glu Glu Arg Glu Thr Lys Thr Pro Glu Cys Pro Ser His
            245             250             255

Thr Gln Pro Leu Gly Val Phe Leu Phe Pro Pro Lys Pro Lys Asp Thr
        260             265             270

Leu Met Ile Ser Arg Thr Pro Glu Val Thr Cys Val Val Val Asp Val
        275             280             285

Ser Gln Glu Asp Pro Glu Val Gln Phe Asn Trp Tyr Val Asp Gly Val
        290             295             300

Glu Val His Asn Ala Lys Thr Lys Pro Arg Glu Glu Gln Phe Asn Ser
305             310             315             320

Thr Tyr Arg Val Val Ser Val Leu Thr Val Leu His Gln Asp Trp Leu
            325             330             335

Asn Gly Lys Glu Tyr Lys Cys Lys Val Ser Asn Lys Gly Leu Pro Ser
            340             345             350

Ser Ile Glu Lys Thr Ile Ser Lys Ala Lys Gly Gln Pro Arg Glu Pro
        355             360             365

Gln Val Tyr Thr Leu Pro Pro Ser Gln Glu Glu Met Thr Lys Asn Gln
        370             375             380

Val Ser Leu Thr Cys Leu Val Lys Gly Phe Tyr Pro Ser Asp Ile Ala
385             390             395             400

Val Glu Trp Glu Ser Asn Gly Gln Pro Glu Asn Asn Tyr Lys Thr Thr
            405             410             415

Pro Pro Val Leu Asp Ser Asp Gly Ser Phe Phe Leu Tyr Ser Arg Leu
            420             425             430

Thr Val Asp Lys Ser Arg Trp Gln Glu Gly Asn Val Phe Ser Cys Ser
        435             440             445

Val Met His Glu Ala Leu His Asn His Tyr Thr Gln Lys Ser Leu Ser
        450             455             460

Leu Ser Leu Gly Lys
465

<210> SEQ ID NO 14
<211> LENGTH: 1407
<212> TYPE: DNA
<213> ORGANISM: Artificial Sequence
<220> FEATURE:
<223> OTHER INFORMATION: nucleotides sequence of FceRIa ECD-hinge-Fc3
```

<400> SEQUENCE: 14

```
atggacgcca tgctgagagg cctgtgctgt gtgctgctgc tgtgcggcgc cgtgttcgtg      60
tcccctagcc acgccgtgcc ccagaagccc aaggtgagcc tgaaccctcc ctggaacaga     120
atcttcaagg gcgagaacgt gaccctgacc tgcaacggca caacttctt cgaggtgagc      180
agcaccaagt ggttccacaa tggcagcctg agcgaggaga ccaacagctc cctgaacatc     240
gtgaacgcca gttcgagga cagcggcgag tacaagtgcc agcaccagca ggtgaacgag      300
agcgagcccg tgtacctgga ggtgttcagc gactggctgc tgctgcaggc cagcgccgag     360
gtggtgatgg agggccagcc cctgttcctg agatgccacg gctggagaaa ctgggacgtg     420
tacaaggtga tctactacaa ggatggcgag gccctgaagt actggtacga gaaccacaac     480
atctccatca ccaacgccac cgtggaggac agcggcacct actactgcac aggcaaggtg     540
tggcagctgg actacgagag cgagcccctg aacatcaccg tgatcaaggc tcccagagag     600
aagtactggc tgcaggccca gccccaggcc gagggcagcc tggctaaggc caccacagct     660
cccgccacca ccaggaacac cggcagagga ggcgaggaaa agaaaggaag caaggagaag     720
gaggagcagg aggaaagaga aaccaagacc cccgagtgcc ccagccacac ccagcccctg     780
ggcgtgttcc tgttcccccc caagcccaag gacaccctga tgatcagcag aaccccccgag    840
gtgacctgcg tggtcgtgga tgtgagccag gaagatcccg aagtgcagtt caactggtac     900
gtggatggcg tggaagtgca caacgccaag accaagccca gagaagagca gttcaactcc     960
acctacagag tggtgagcgt gctgaccgtg ctgcaccagg actggctgaa cggcaaggag    1020
tacaagtgca aggtgtccaa caaaggcctg cccagctcca tcgagaagac catcagcaaa    1080
gccaaaggcc agccccagaga accccaggtg tacaccctgc ctcccagcca ggaagagatg    1140
accaagaacc aggtgtccct gacctgctg gtgaaaggct tctacccag cgacatcgcc     1200
gtggagtggg aaagcaacgg ccagcccgag aacaattaca agacaacccc tcccgtgctg    1260
gatagcgatg gcagcttctt tctgtacagc agactgaccg tggacaagag cagatggcag    1320
gaaggcaacg tgttcagctg cagcgtgatg cacgaagccc tgcacaacca ctacacccag    1380
aagagcctgt ccctgagcct gggcaag                                        1407
```

<210> SEQ ID NO 15
<211> LENGTH: 406
<212> TYPE: PRT
<213> ORGANISM: Artificial Sequence
<220> FEATURE:
<223> OTHER INFORMATION: human a-2,6 sialic acid transferase

<400> SEQUENCE: 15

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Lys Gly
                20                  25                  30

Ser Tyr Tyr Asp Ser Phe Lys Leu Gln Thr Lys Glu Phe Gln Val Leu
            35                  40                  45

Lys Ser Leu Gly Lys Leu Ala Met Gly Ser Asp Ser Gln Ser Val Ser
        50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
```

```
            100                 105                 110
Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
        130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Tyr Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 16
<211> LENGTH: 1218
<212> TYPE: DNA
<213> ORGANISM: Artificial Sequence
<220> FEATURE:
<223> OTHER INFORMATION: nucleotides sequence of human a-2,6 sialic acid
      transferase

<400> SEQUENCE: 16
atgatccaca ccaacctgaa gaagaagttc agctgctgcg tgctggtgtt cctgctgttc        60
gccgtgatct gcgtgtggaa ggagaagaag aaaggcagct actacgacag cttcaagctg       120
cagaccaagg agttccaggt gctgaagagc ctgggcaagc tggccatggg cagcgacagc       180
cagagcgtgt ccagctcctc cacccaggat ccccacagag cagacagac  cctgggcagc       240 ctgagaggcc tggccaaggc caagcccgag gccagcttcc aggtgtggaa caaggacagc       300
```

```
agcagcaaga acctgatccc cagactgcag aagatctgga agaactacct gagcatgaac    360
aagtacaagg tgagctacaa aggacccgga cccggcatca agttcagcgc cgaggccctg    420
aggtgccacc tgagagacca cgtgaacgtg agcatggtgg aagtgaccga cttccccttc    480
aacaccagcg agtgggaagg ctacctgccc aaggagagca tcaggaccaa ggctggcccc    540
tggggcagat gcgccgtggt gagcagcgct ggcagcctga agagctccca gctgggcaga    600
gagatcgacg accacgatgc cgtgctgagg ttcaatggcg ctcccaccgc caacttccag    660
caggacgtgg gcaccaagac cacaatccgg ctgatgaaca gccagctggt gacaaccgag    720
aagcggttcc tgaaggacag cctgtacaac gagggcatcc tgatcgtgtg ggatcccagc    780
gtgtaccaca gcgacatccc caagtggtac cagaatcccg actacaactt cttcaacaac    840
tacaagacct atagaaagct gcaccccaac cagcccttct acatcctgaa gccccagatg    900
ccctgggagc tgtgggacat cctgcaggag atcagccctg aagagatcca gcccaaccct    960
ccctccagcg gcatgctggg cattatcatc atgatgaccc tgtgcgacca ggtggacatc   1020
tacgagttcc tgcccagcaa gagaaagacc gacgtgtgct actactatca gaagttcttc   1080
gacagcgcct gcaccatggg cgcctaccac cccctgctgt acgagaagaa cctggtgaag   1140
cacctgaacc agggcaccga cgaggacatc tacctgctgg gcaaagccac cctgcccggc   1200
ttcagaacca tccactgc                                                  1218
```

<210> SEQ ID NO 17
<211> LENGTH: 30
<212> TYPE: PRT
<213> ORGANISM: Artificial Sequence
<220> FEATURE:
<223> OTHER INFORMATION: IgD hinge variant
<220> FEATURE:
<221> NAME/KEY: Xaa is Lys or Gly
<222> LOCATION: (12)..(12)
<220> FEATURE:
<221> NAME/KEY: Xaa is Glu, Gly, or Ser
<222> LOCATION: (13)..(13)

<400> SEQUENCE: 17

Arg Asn Thr Gly Arg Gly Gly Glu Glu Lys Lys Xaa Xaa Lys Glu Lys
1               5                   10                  15

Glu Glu Gln Glu Glu Arg Glu Thr Lys Thr Pro Glu Cys Pro
            20                  25                  30

<210> SEQ ID NO 18
<211> LENGTH: 49
<212> TYPE: PRT
<213> ORGANISM: Artificial Sequence
<220> FEATURE:
<223> OTHER INFORMATION: IgD hinge variant
<220> FEATURE:
<221> NAME/KEY: Xaa is Lys or Gly
<222> LOCATION: (31)..(31)
<220> FEATURE:
<221> NAME/KEY: Xaa is Glu, Gly, or Ser
<222> LOCATION: (32)..(32)

<400> SEQUENCE: 18

Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Glu Lys Lys Xaa Xaa
            20                  25                  30

Lys Glu Lys Glu Glu Gln Glu Glu Arg Glu Thr Lys Thr Pro Glu Cys
        35                  40                  45

Pro

<210> SEQ ID NO 19
<211> LENGTH: 30
<212> TYPE: PRT
<213> ORGANISM: Artificial Sequence
<220> FEATURE:
<223> OTHER INFORMATION: IgD hinge

<400> SEQUENCE: 19

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro
            20                  25                  30

<210> SEQ ID NO 20
<211> LENGTH: 425
<212> TYPE: PRT
<213> ORGANISM: Artificial Sequence
<220> FEATURE:
<223> OTHER INFORMATION: FceRIa ECD-hinge-Fc1

<400> SEQUENCE: 20

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Gly Glu Glu Lys Lys Lys
            180                 185                 190

Glu Lys Glu Lys Glu Glu Gln Glu Glu Arg Glu Thr Lys Thr Pro Glu
        195                 200                 205

Cys Pro Ser His Thr Gln Pro Leu Gly Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

```
Gln Phe Asn Ser Thr Tyr Arg Val Val Ser Val Leu Thr Val Leu His
            275                 280                 285

Gln Asp Trp Leu Asn Gly Lys Glu Tyr Lys Cys Lys Val Ser Asn Lys
290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
            420                 425

<210> SEQ ID NO 21
<211> LENGTH: 425
<212> TYPE: PRT
<213> ORGANISM: Artificial Sequence
<220> FEATURE:
<223> OTHER INFORMATION: FceRIa ECD-hinge-Fc2

<400> SEQUENCE: 21

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Glu Glu Lys Lys Gly
            180                 185                 190

Ser Lys Glu Lys Glu Glu Gln Glu Glu Arg Glu Thr Lys Thr Pro Glu
        195                 200                 205
```

Cys Pro Ser His Thr Gln Pro Leu Gly Val Phe Leu Phe Pro Pro Lys
      210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
            420                 425

<210> SEQ ID NO 22
<211> LENGTH: 444
<212> TYPE: PRT
<213> ORGANISM: Artificial Sequence
<220> FEATURE:
<223> OTHER INFORMATION: FceRIa ECD-hinge-Fc3

<400> SEQUENCE: 22

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

```
Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Ala Gln Pro Gln Ala Glu Gly Ser Leu Ala Lys Ala
                180                 185                 190

Thr Thr Ala Pro Ala Thr Thr Arg Asn Thr Gly Arg Gly Gly Glu Glu
            195                 200                 205

Lys Lys Gly Ser Lys Glu Lys Glu Gln Glu Glu Arg Glu Thr Lys
        210                 215                 220

Thr Pro Glu Cys Pro Ser His Thr Gln Pro Leu Gly Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

EXTRACELLULAR DOMAIN OF ALPHA SUBUNIT OF IgE Fc RECEPTOR, PHARMACEUTICAL COMPOSITION COMPRISING SAME AND METHOD FOR PRODUCING SAME

CROSS REFERENCE TO RELATED APPLICATIONS

This application is a National Stage of International Application No. PCT/KR2019/000274 filed Jan. 8, 2019, claiming priority based on Korean Patent Application No. 10-2018-0002248 filed Jan. 8, 2018.

INCORPORATION BY REFERENCE OF SEQUENCE LISTING

The instant application contains a Sequence Listing which has been filed electronically in txt format and is hereby incorporated by reference in its entirety. Said txt copy, created on Jul. 1, 2020, is named Q255662SubstituteSequenceListingasfiled932020.txt and is 35.6 KB in size.

TECHNICAL FIELD

The present invention relates to modified IgE Fc receptors and uses thereof.

BACKGROUND ART

Allergic diseases, such as allergic rhinitis, atopic dermatitis, and food allergy, including asthma are spreading at a high rate in industrialized and westernized modern societies, and development of anaphylaxis, a severe allergic disease, is also increasing. These chronic immune diseases severely impair individuals' quality of life and socioeconomic costs are soaring accordingly. Thus, there is a desperate need for measures to overcome such diseases.

Most allergic diseases are caused by an excessive immune response of immunoglobulin E (IgE). IgE is an antibody that is present in serum at a very low concentration under a normal condition. IgE is also usually produced by innocuous antigens. There is a case where the number of IgE is increased without any particular stimulus. Such a case may lead to allergic diseases. The abnormally increased number of IgE can bind to high-affinity IgE Fc receptors (FcεRIs) which are expressed on the surface of mast cells, basophils, and the like. Such binding causes mast cells or basophils to release chemical mediators such as histamine, leukotriene, prostaglandin, bradykinin, and platelet-activating factors. Release of these chemical mediators results in allergic symptoms. In particular, allergic diseases may exhibit worsened symptoms due to the binding between IgE and FcεRI. FcεRI-expressing cells are known to increase in allergic patients.

Currently, various methods, such as allergen avoidance, administration of anti-allergic drugs, modulation of IgE synthesis in the body, and development of anti-IgE antibodies, have been proposed to treat allergic diseases. However, therapeutic methods known so far have many drawbacks, such as inability to cure an underlying cause of allergy, insufficient drug efficacy, and occurrence of serious side effects.

In addition, immunoglobulin compositions capable of binding to IgE and FcγRIIb with high affinity and inhibiting cells expressing IgE have been studied (KR10-1783272B1). Such compositions have been reported to be useful for treating IgE-mediated disorders including allergy and asthma. In addition, omalizumab (trade name: XOLAIR®), which targets an Fc portion of an IgE antibody, has been developed and used as a therapeutic agent for intractable severe asthma and intractable urticaria.

However, a high-dose administration of omalizumab to maintain therapeutic effects leads to a high cost burden, and side effects such as angioedema and anaphylactic reaction (The Journal of Clinical Investigation Volume 99, Number 5, March 1997, 915-925). Besides, from the post-marketing results, allergic granulomatous vasculitis and idiopathic severe thrombocytopenia have been reported. Accordingly, there is a growing need for development of therapeutic agents capable of effectively treating allergic diseases without side effects.

Technical Problem

An object of the present invention is to provide a polypeptide dimeric protein for treating an IgE-mediated allergic disease. Another object of the present invention is to provide a nucleic acid molecule encoding the protein, an expression vector containing the nucleic acid molecule, and a host cell containing the expression vector. Yet another object of the present invention is to provide a method for preparing the polypeptide dimer.

Solution to Problem

In order to achieve the above objects, there is provided a polypeptide dimer, comprising two monomers, each of which contains an extracellular domain of an alpha subunit of an IgE Fc receptor. The monomer contains a modified Fc region, and the modified Fc region and the extracellular domain of the alpha subunit of the IgE Fc receptor are linked via a hinge of an IgD antibody. In another aspect, there is provided a pharmaceutical composition for treating or preventing an allergic disease, comprising the polypeptide dimer as an active ingredient.

Advantageous Effects of Invention

The polypeptide dimeric protein according to the present invention not only has excellent safety and persistence in the body as compared with conventionally used anti-IgE antibodies, but also binds to IgE very strongly due to having a binding capacity to IgE which is 70-fold higher than the conventionally used anti-IgE antibody, omalizumab, which allows an extended administration cycle. In addition, the polypeptide dimeric protein according to the present invention is a substance obtained by applying a modified Fc, which has IgE alone as a single target and does not bind to an Fc gamma receptor, and thus lacks antibody dependent cellular cytotoxicity (ADCC) and complement dependent cytotoxicity (CDC) functions.

Therefore, unlike conventional anti-IgE antibodies containing an IgG1 Fc region, the polypeptide dimeric protein does not bind to an Fc gamma receptor, and thus can inhibit release of mediators caused by being bound to the Fc gamma receptor on the surface of mast cells, so that severe side effects such as occurrence of anaphylaxis which can be caused by binding between IgG1 and Fc gamma receptor III on mast cells can be minimized. Therefore, the polypeptide dimeric protein according to the present invention can be utilized as a new pharmaceutical composition which can replace therapeutic agents containing a conventional anti-IgE antibody.

BRIEF DESCRIPTION OF DRAWINGS

FIGS. 1A-1C show results of SDS-PAGE and gel isoelectric focusing (IEF) for proteins produced in each cell line. Here, it can be seen that a truncated form is not generated at both reducing and non-reducing conditions, and that a content of acidic proteins is increased due to an increase in sialic acid content caused by introduction of a sialic acid transferase gene.

FIG. 2 illustrates SDS-PAGE results for non-reduced and reduced forms of the polypeptide dimeric protein according to an embodiment of the present invention. In particular, it can be seen that the polypeptide dimer has high purity even in culture supernatant which corresponds to Input.

FIG. 3 illustrates a graph showing a binding ability of omalizumab to IgE. The graph shows results obtained by immobilizing omalizumab and analyzing a binding ability thereof depending on IgE concentrations treated.

FIG. 4 illustrates a graph showing a binding ability, to IgE, of the polypeptide dimeric protein according to an embodiment of the present invention. The graph shows results obtained by immobilizing the dimeric protein and analyzing a binding ability thereof depending on IgE concentrations treated.

FIGS. 5A-5E illustrate results obtained by identifying interactions of the polypeptide dimeric protein (IgE$_{TRAP}$), an embodiment of the present invention, and omalizumab with IgG receptors FcγRI (FIG. 5A), FcγRIIA (FIG. 5B), FcγRIIB (FIG. 5C), FcγRIIIA (FIG. 5D), and FcγRIIIB (FIG. 5E) by bio-layer interferometry (BLI) assay.

FIG. 6 illustrates a graph obtained by quantifying a binding capacity between IgE$_{TRAP}$ and IgG receptors, and between omalizumab and IgG receptors.

FIG. 7 illustrates a graph showing an inhibitory ability, on activity of mouse-derived mast cells, of the polypeptide dimeric protein (IgE$_{TRAP}$) according to an embodiment of the present invention depending on concentrations thereof.

FIG. 8 illustrates a graph showing a comparison between inhibitory abilities, on activity of human FcεRI-expressing mouse-derived mast cells, of the polypeptide dimeric protein (IgE$_{TRAP}$) according to an embodiment of the present invention and XOLAIR® (omalizumab) depending on concentrations thereof.

FIG. 9 illustrates a graph showing administration effects of the polypeptide dimeric protein according to an embodiment of the present invention in a food allergy model.

DETAILED DESCRIPTION OF INVENTION

The present invention relates to a polypeptide dimer, comprising two monomers, each of which contains an extracellular domain (FcεRIa-ECD) of an alpha subunit of an IgE Fc receptor, in which the monomer contains a modified Fc region, and the modified Fc region and the FcεRIa-ECD are linked via a hinge of an IgD antibody.

As used herein, the term "IgE" means an antibody protein known as immunoglobulin E. IgE has an affinity to mast cells, blood basophils, or the like. In addition, reaction between an IgE antibody and an antigen (allergen) corresponding thereto causes an inflammatory reaction. In addition, IgE is known to be an antibody that causes anaphylaxis which occurs due to sudden secretion of mast cells or basophils.

As used herein, the term "IgE Fc receptor" is also referred to as Fcε receptor and binds to an Fc portion of IgE. There are two types for the receptor. The receptor having high affinity to IgE Fc is called Fcε receptor I (FcεRI). The receptor having low affinity to IgE Fc is called Fcε receptor II (FcεRII). FcεRI is expressed in mast cells and basophils. In a case where IgE antibodies bound to FcεRI are cross-linked by polyvalent antigens, degranulation occurs in mast cells or basophils, thereby releasing various chemical transmitter substances including histamine. This release leads to an immediate allergic reaction.

The FcεRI is a membrane protein composed of one α chain, one β chain, and two γ chains linked by a disulfide bond. Among these chains, a portion to which IgE binds is the α chain (FcεRIa). FcεRIα has a size of about 60 kDa, and is composed of a hydrophobic domain existing inside the cell membrane and a hydrophilic domain existing outside the cell membrane. In particular, IgE binds to an extracellular domain of the α chain.

Specifically, the alpha subunit of the IgE Fc receptor may have the amino acid sequence set forth in NP_001992.1. In addition, the extracellular domain (FcεRIa-ECD) of the alpha subunit of the IgE Fc receptor may have the amino acid sequence of SEQ ID NO: 1. In the present specification, the extracellular domain of the alpha subunit of the IgE Fc receptor may be a fragment or variant of the extracellular domain of the alpha subunit of the IgE Fc receptor, as long as the fragment or variant is capable of binding to IgE.

The variant may be prepared through a method of substituting, deleting, or adding one or more proteins in the wild-type FcεRIa-ECD (extracellular domain), as long as the method does not alter a function of the α chain of FcεRI. Such various proteins or peptides may be 90%, 91%, 92%, 93%, 94%, 95%, 96%, 97%, 98%, 99% or more identical to the amino acid sequence of SEQ ID NO: 1. In addition, the FcεRIa-ECD of SEQ ID NO: 1 may be encoded by a polynucleotide having the sequence of SEQ ID NO: 5.

In addition, as used herein, the term "modified Fc region" means a region in which a part of an Fc portion of an antibody has been modified. Here, the term "Fc region" refers to a protein which contains heavy chain constant region 2 (CH2) and heavy chain constant region 3 (CH3) of an immunoglobulin, and does not contain variable regions of heavy and light chains and light chain constant region 1 (CH1) of an immunoglobulin. In particular, the modified Fc region means a region obtained by substituting some amino acids in the Fc region or by combining different types of Fc regions. Specifically, the modified Fc region may have the amino acid sequence of SEQ ID NO: 2. In addition, the modified Fc region of SEQ ID NO: 2 may be encoded by a polynucleotide having the sequence of SEQ ID NO: 6.

In addition, the "modified Fc region" of the present invention may be in the form of having sugar chains in a native form, increased sugar chains relative to a native form, or decreased sugar chains relative to a native form, or may be in the form of being sugar chain-removed. Immunoglobulin Fc sugar chains may be modified by conventional methods such as chemical methods, enzymatic methods, and genetic engineering methods using microorganisms.

Here, the "modified Fc region" of the present invention may be a region that lacks antibody dependent cellular cytotoxicity (ADCC) and complement dependent cytotoxicity (CDC) functions due to having no binding site for FcγR or C1q. In addition, the modified Fc region and the FcεRIa-ECD may be linked via a hinge of an IgD antibody. The hinge of the IgD antibody is composed of 64 amino acids, and may selectively contain 20 to 60 consecutive amino acids, 25 to 50 consecutive amino acids, or 30 to 40 amino acids. In an embodiment, the hinge of the IgD antibody may be composed of 30 or 49 amino acids as shown below. In addition, the hinge of the IgD antibody may be a hinge variant obtained by modifying the hinge region, in which the hinge may contain at least one cysteine. Here, the hinge variant may be obtained by modifying some in a hinge sequence of the IgD antibody in order to minimize generation of truncated forms during a protein production process.

In an embodiment, the hinge may contain the following sequence:

Arg Asn Thr Gly Arg Gly Gly Glu Glu Lys Lys Xaa1 Xaa2 Lys Glu Lys Glu Glu Gln Glu Glu Arg Glu Thr Lys Thr Pro Glu Cys Pro (SEQ ID NO: 17), where Xaa1 may be Lys or Gly, and Xaa2 may be Glu, Gly, or Ser. Specifically, the hinge may have the amino acid sequence of SEQ ID NO: 3 or SEQ ID NO: 19, thereby minimizing generation of truncated forms during a protein production process.

In another embodiment, the hinge may contain the following sequence:

Ala Gln Pro Gln Ala Glu Gly Ser Leu Ala Lys Ala Thr Thr Ala Pro Ala Thr Thr Arg Asn Thr Gly Arg Gly Gly Glu Glu Lys Lys Xaa3 Xaa4 Lys Glu Lys Glu Glu Gln Glu Glu Arg Glu Thr Lys Thr Pro Glu Cys Pro (SEQ ID NO: 18), where Xaa3 may be Lys or Gly, and Xaa4 may be Glu, Gly, or Ser. Specifically, the hinge may have the amino acid sequence of SEQ ID NO: 4, thereby minimizing generation of truncated forms during a protein production process.

In particular, in the hinge having the sequence of SEQ ID NO: 4, at least one of Thr's may be glycosylated. Specifically, among the amino acids of SEQ ID NO: 18, the $13^{th}$, $14^{th}$, $18^{th}$, or $19^{th}$ Thr's may be glycosylated. Preferably, all four amino acids may be glycosylated. Here, the glycosylation may be O-glycosylation.

In addition, as described above, the polypeptide dimer provided by the present invention may be in a form in which two monomers are bound to each other and each monomer is obtained by binding between an extracellular domain of an alpha subunit of an IgE Fc receptor and a modified Fc region. The polypeptide dimer may be in a form in which the same two monomers are bound to each other by cysteine located at a hinge site. In addition, the polypeptide dimer may be in a form in which two different monomers are bound to each other. For example, in a case where the two monomers are different from each other, the polypeptide dimer may be in a form in which one monomer contains the extracellular domain of the alpha subunit of the IgE Fc receptor, and the other monomer contains a fragment of the extracellular domain of the alpha subunit of the IgE Fc receptor. Here, an embodiment of the monomer may have the amino acid sequence of SEQ ID NO: 20, SEQ ID NO: 21, or SEQ ID NO: 22.

In addition, the polypeptide dimer provided by the present invention exhibits a binding capacity to IgE which is 10- to 100-fold, 20- to 90-fold, 20- to 70-fold, 30- to 70-fold, or 40- to 70-fold higher than omalizumab, an anti-IgE antibody, and may preferably exhibit a binding capacity to IgE which is 70-fold higher than omalizumab.

In yet another aspect of the invention, there is provided a polynucleotide encoding a monomer that contains an extracellular domain of an alpha subunit of an IgE Fc receptor to which a modified Fc region is bound.

Meanwhile, the polynucleotide may additionally contain a signal sequence or a leader sequence. As used herein, the term "signal sequence" means a nucleic acid encoding a signal peptide that directs secretion of a target protein. The signal peptide is translated and then cleaved in a host cell. Specifically, the signal sequence of the present invention is a nucleotide encoding an amino acid sequence that initiates protein translocation across the endoplasmic reticulum (ER) membrane. Useful signal sequences in the present invention include antibody light chain signal sequences, for example, antibody 14.18 (Gillies et al., J. Immunol. Meth 1989. 125:191-202), antibody heavy chain signal sequences, for example, the MOPC141 antibody heavy chain signal sequence (Sakano et al., Nature, 1980. 286:676-683), and other signal sequences known in the art (see, for example, Watson et al., Nucleic Acid Research, 1984. 12:5145-5164).

The signal sequences are well known in the art for their characteristics. The signal sequences typically contain 16 to 30 amino acid residues, and may contain greater or fewer amino acid residues. A typical signal peptide consists of three regions which are a basic N-terminal region, a central hydrophobic region, and a more polar C-terminal region. The central hydrophobic region contains 4 to 12 hydrophobic residues that immobilize the signal sequence through the membrane lipid bilayer during translocation of an immature polypeptide.

After initiation, a signal sequence is cleaved in the lumen of ER by cellular enzymes commonly known as signal peptidases. Here, the signal sequence may be a secretory signal sequence for tissue plasminogen activator (tPA), Herpes simplex virus glycoprotein D (HSV gD), or growth hormone. Preferably, secretory signal sequences used in higher eukaryotic cells, including mammals and the like, can be used. In addition, the secretory signal sequence may be substituted with a codon having a high frequency of expression in a host cell, and used.

Meanwhile, the extracellular domain monomer of the alpha subunit of the IgE Fc receptor to which a signal sequence and a modified Fc region are bound, may have the amino acid sequence of SEQ ID NO: 11 or SEQ ID NO: 13. The proteins of SEQ ID NO: 11 and SEQ ID NO: 13 may be encoded by polynucleotides having the sequences of SEQ ID NO: 12 and SEQ ID NO: 14, respectively.

In still yet another aspect of the present invention, there is provided an expression vector loaded with a polynucleotide encoding the monomer. Here, the polynucleotide may have the sequence of SEQ ID NO: 12 or SEQ ID NO: 14.

As used herein, the term "vector" is intended to be introduced into a host cell and to be capable of being recombined with a host cell genome and inserted thereinto. Alternatively, the vector is an episome and is understood as a nucleic acid unit containing a nucleotide sequence that can be autonomously replicated. The vectors include linear nucleic acids, plasmids, phagemids, cosmids, RNA vectors, viral vectors, and analogs thereof. Examples of the viral vectors include, but are not limited to, retroviruses, adenoviruses, and adeno-associated viruses. In addition, the plasmids may contain a selectable marker such as an antibiotic-resistant gene, and host cells harboring the plasmids may be cultured under selective conditions.

As used herein, the term "genetic expression" or "expression" of a target protein is understood to mean transcription of a DNA sequence, translation of an mRNA transcript, and secretion of a fusion protein product or a fragment thereof. A useful expression vector may be RcCMV (INVITROGEN™, Carlsbad) or a variant thereof. The expression vector may contain human cytomegalovirus (CMV) promoter for promoting continuous transcription of a target gene in mammalian cells, and a bovine growth hormone polyadenylation signal sequence for increasing a stability level of RNA after transcription.

In still yet another aspect of the present invention, there is provided a host cell into which the expression vector is introduced. As used herein, the term "host cell" refers to a prokaryotic or eukaryotic cell into which a recombinant expression vector can be introduced. As used herein, the terms "transduced", "transformed", and "transfected" means introducing a nucleic acid (for example, a vector) into a cell using techniques known in the art.

Preferred host cells that can be used in the present invention include immortal hybridoma cells, NS/0 myeloma cells, 293 cells, Chinese hamster ovary cells (CHO cells), HeLa cells, human amniotic fluid-derived cells (CapT cells), or COS cells. Preferably, the host cells may be CHO cells. On the other hand, the host cell may be one in which the vector and a vector loaded with a sialic acid transferase gene are introduced. Here, the sialic acid transferase may be 2,3-sialic acid transferase or 2,6-sialic acid transferase. Here, the 2,6-sialic acid transferase may have the amino acid sequence of SEQ ID NO: 15.

In still yet another aspect of the present invention, there is provided a pharmaceutical composition for treating or preventing an allergic disease, comprising the polypeptide dimer as an active ingredient.

In the present specification, the term "allergic disease" means a pathological symptom caused by an allergic reaction mediated by mast cell activation such as mast cell degranulation. Such allergic diseases include food allergy, atopic dermatitis, asthma, allergic rhinitis, allergic conjunctivitis, allergic dermatitis, allergic contact dermatitis, anaphylaxis, urticaria, pruritus, insect allergy, chronic idiopathic urticaria, drug allergy, and the like. In particular, the allergic diseases may be IgE-mediated.

In the composition for treating or preventing allergic disease of the present invention, an active ingredient may be contained in any amount (effective amount) depending on use, formulation, blending purpose, and the like, as long as the active ingredient can exhibit anti-allergic activity. A typical effective amount of the active ingredient will be determined within a range of 0.001% by weight to 20.0% by weight based on a total weight of the composition. Here, "effective amount" refers to an amount of an active ingredient which is capable of inducing an anti-allergic effect. Such an effective amount can be determined experimentally within the ordinary skill of those skilled in the art.

Here, the pharmaceutical composition may further contain a pharmaceutically acceptable carrier. For the pharmaceutically acceptable carrier, any carrier can be used as long as the carrier is a non-toxic substance suitable for delivery to a patient. Distilled water, alcohol, fat, wax, and an inert solid may be contained as carriers. Pharmaceutically acceptable adjuvants (buffers and dispersants) may also be contained in the pharmaceutically composition.

Specifically, the pharmaceutical composition of the present invention contains, in addition to an active ingredient, a pharmaceutically acceptable carrier, and may be made into an oral or parenteral formulation depending on a route of administration by a conventional method known in the art. Here, the term "pharmaceutically acceptable" means not having more toxicity than a subject to be applied (prescribed) can accommodate without inhibiting activity of the active ingredient.

In a case where the pharmaceutical composition of the present invention is made into an oral formulation, the pharmaceutical composition may be made into formulations such as powders, granules, tablets, pills, sugar coating tablets, capsules, liquids, gels, syrups, suspensions, and wafers, together with suitable carriers, in accordance with methods known in the art. Here, examples of suitable pharmaceutically acceptable carriers can include sugars such as lactose, glucose, sucrose, dextrose, sorbitol, mannitol, and xylitol, starches such as corn starch, potato starch, and wheat starch, celluloses such as cellulose, methylcellulose, ethylcellulose, sodium carboxymethyl cellulose, and hydroxypropylmethyl cellulose, polyvinyl pyrrolidone, water, methylhydroxybenzoate, propylhydroxybenzoate, magnesium stearate, mineral oil, malt, gelatin, talc, polyol, vegetable oil, and the like. In a case of being made into preparations, the preparations can be carried out, as necessary, by including diluents and/or excipients such as a filler, an extender, a binder, a wetting agent, a disintegrant, and a surfactant.

In a case where the pharmaceutical composition of the present invention is made into a parenteral formulation, the pharmaceutical composition may be made into preparations in the form of injections, transdermal drugs, nasal inhalers, and suppositories, together with suitable carriers, in accordance with methods known in the art. In a case of being prepared into injections, sterilized water, ethanol, polyol such as glycerol and propylene glycol, or a mixture thereof may be used as a suitable carrier. For the carrier, isotonic solutions such as Ringer's solution, phosphate buffered saline (PBS) containing triethanolamine, sterile water for injection, and 5% dextrose, and the like may be preferably used.

Preparation of the pharmaceutical composition is known in the art and specifically, reference can be made to Remington's Pharmaceutical Sciences (19th ed., 1995) and the like. The document is considered part of the present specification.

A preferable daily dosage of the pharmaceutical composition of the present invention is ranged from 0.01 ug/kg to 10 g/kg, and preferably from 0.01 mg/kg to 1 g/kg, depending on the patient's condition, body weight, sex, age, disease severity, or route of administration. Administration may be carried out once or several times a day. Such a dosage should in no way be interpreted as limiting the scope of the present invention.

The subject to which the composition of the present invention can be applied (prescribed) is a mammal and a human, with a human being particularly preferred. The composition for anti-allergy of the present invention may further comprise, in addition to the active ingredient, any compound or natural extract, on which safety has already been verified and which is known to have anti-allergic activity, for the purpose of raising and reinforcing the anti-allergic activity.

In another aspect of the present invention, there is provided a food composition for ameliorating and alleviating an allergic symptom, comprising the polypeptide dimer as an active ingredient.

Here, the polypeptide dimer may be bound to an appropriate delivery unit for efficient delivery into the intestines. The food composition of the present invention may be prepared in any form and may be, for example, prepared in the form of beverages such as tea, juice, carbonated beverage, and ionic beverage, processed dairy products such as milk and yogurt, health functional food preparations such as tablets, capsules, pills, granules, liquids, powders, flakes, pastes, syrups, gels, jellies, and bars, or the like. In addition, the food composition of the present invention may fall within any product category in legal or functional classification as long as the food composition complies with the enforcement regulations at the time of being manufactured and distributed. For example, the food composition may be a health functional food according to the Health Functional Foods Act, or may fall within confectioneries, beans, teas, beverages, special-purpose foods, or the like according to each food type in the Food Code of Food Sanitation Act (standards and specifications for food, notified by Food and Drug Administration). With regard to other food additives that may be contained in the food composition of the present invention, reference can be made to the Food Code or the Food Additive Code according to the Food Sanitation Act.

In yet another aspect of the present invention, there is provided a method for producing a polypeptide dimer, comprising a step of culturing a host cell into which a polynucleotide encoding a monomer and a sialic acid transferase gene have been introduced; and a step of recovering a polypeptide dimer.

Here, the polynucleotide encoding the monomer may be introduced into the host cell in the form of being loaded on an expression vector. In addition, the sialic acid transferase gene may be introduced into the host cell in the form of being loaded on a vector.

First, a step of introducing, into a host cell, a vector loaded with a polynucleotide encoding a monomer and a vector loaded with a sialic acid transferase gene is carried out. Here, the sialic acid transferase may be 2,3-sialic acid transferase or 2,6-sialic acid transferase.

Next, a step of culturing the transformed cell is carried out.

Finally, a step of recovering a polypeptide dimer is carried out. Here, the polypeptide dimer may be purified from a culture medium or a cell extract. For example, after obtaining supernatant of a culture medium in which the polypeptide dimer is secreted, the supernatant may be concentrated using a commercially available protein concentration filter, for example, an AMICON® or MILLIPORE® PELLICON® ultrafiltration unit. Then, the concentrate may be purified by methods known in the art. For example, the purification may be achieved using a matrix coupled to protein A.

In still yet another aspect of the present invention, there is provided a polypeptide dimer produced by the above-described method for producing a dimer.

Here, the polypeptide dimer has a high sialic acid content, and thus has a very high content of acidic proteins relative to the theoretical pI value.

In still yet another aspect of the present invention, there is provided a pharmaceutical composition for treating or preventing an allergic disease, comprising, as an active ingredient, the polypeptide dimer produced by the above-described method for producing a dimer.

In still yet another aspect of the present invention, there is provided a food composition for ameliorating or alleviating an allergic symptom comprising, as an active ingredient, the polypeptide dimer produced by the above-described method for producing a dimer.

In still yet another aspect of the present invention there is provided a method for treating or preventing an allergic disease, comprising a step of administering to a subject a polypeptide dimer that contains two monomers, each of which contains the extracellular domain (FcεRIa-ECD) of the alpha subunit of the IgE Fc receptor.

The subject may be a mammal, preferably a human. Here, administration may be achieved orally or parenterally. Here, parenteral administration may be performed by methods such as subcutaneous administration, intravenous administration, mucosal administration, and muscular administration.

Hereinafter, the present invention will be described in more detail with reference to the following examples. However, the following examples are intended to merely illustrate the present invention, and the scope of the present invention is not limited only thereto.

Example 1. Preparation of Polypeptide Containing FcεRIα-ECD and Modified Fc Region A C-terminal modified polypeptide of the extracellular domain (FcεRIα-ECD) of the alpha subunit of the IgE Fc receptor was prepared according to the method disclosed in U.S. Pat. No. 7,867,491.

First, in order to express a protein (FcεRIαECD-Fc1), a protein (FcεRIαECD-Fc2), and a protein (FcεR1αECD-Fc3), in which the extracellular domain of the α-chain of FcεRI having the amino acid sequence of SEQ ID NO: 1 and the modified immunoglobulin Fc of SEQ ID NO: 2 are linked via a hinge of SEQ ID NO: 19, a hinge of SEQ ID NO: 3, and a hinge of SEQ ID NO: 4, respectively, cassettes obtained by linking the gene encoding each protein were cloned into the pAD15 vectors (Genexin, Inc.) to construct FcεRIαECD-Fc protein expression vectors. Then, each of the expression vectors was transduced into CHO DG44 cells (from Dr. Chasm, Columbia University, USA).

Here, at the time of being transduced into the cell line, an expression vector obtained by cloning an α-2,6-sialic acid transferase gene into the pCI Hygro vector (INVITROGEN™) was simultaneously transduced to separately prepare cell lines which are capable of expressing FcεRIαECD-Fc2ST and FcεRIα ECD-Fc3ST proteins to which sialic acid is added.

As a primary screening procedure, HT selection was carried out using 5-hydroxytryptamine (HT)-free 10% dFBS medium (GIBCO™, USA, 30067-334), MEMa medium (GIBCO™, 12561, USA, Cat No. 12561-049), and HT+ medium (GIBCO™, USA, 11067-030). Then, methotrexate (MTX) amplification was performed using HT-selected clones to amplify productivity using the dihydrofolate reductase (DHFR)-system.

After completion of the MTX amplification, subculture was carried out about 1 to 5 times for cell stabilization for the purpose of evaluation of productivity. Thereafter, unit productivity evaluation of the MTX-amplified cells was performed. The results are shown in Table 1 below.

TABLE 1

| | | | Productivity | | |
| | | | 3-day culture | | Batch |
| Version | Media | MTX concentration | ug/mL | ug/10⁶ cells | culture (mg/ml) |
| --- | --- | --- | --- | --- | --- |
| FcεRIαECD-Fc2 | Ex-cellDHFR | 500 nM | 37.23 | 20.9 | 225 |
| FcεRIαECD-Fc2 + a2,6-ST | | 100 nM | 45.4 | 25.1 | 338.2 |
| FcεRIαECD-Fc3 | | 2 uM | 27.0 | 16.9 | 180.4 |
| FcεRIαECD-Fc3 + a2,6-ST | | 1 uM | 17.5 | 10.2 | 101.7 |

As shown in Table 1, the FcεRIαECD-Fc3 cell line exhibited productivity of 16.9 ug/10⁶ cells after the methotrexate amplification at 2 uM. On the other hand, the FcεRIαECD-Fc3 cell line (FcεRIαECD-Fc3ST) co-transduced with 2,6-sialic acid transferase exhibited productivity of 10.2 ug/10⁶ cells after the methotrexate amplification at 1 uM. In addition, the FcεRIαECD-Fc2 cell line exhibited productivity of 20.9 ug/10⁶ cells under the methotrexate amplification condition at 0.5 uM. In addition, the FcεRIαECD-Fc2 cell line (FcεRIαECD-Fc2ST) co-transduced with 2,6-sialic acid transferase exhibited productivity of 25.1 ug/10⁶ cells after the methotrexate amplification at 0.1 uM. That is, it was identified that the FcεRIαECD-Fc2 cell line co-transfected with 2,6-sialic acid transferase, which had been selected under the methotrexate amplification condition at 0.1 uM, exhibits the most excellent productivity.

Example 2. Purification of FcεRIα ECD Fusion Protein and Identification of Purity Thereof Among the cell lines selected in Example 1 above, i) FcεRIαECD-Fc3, ii) FcεRIαECD-Fc3ST, and iii) FcεRIαECD-Fc2ST were cultured at a 60 ml scale by a batch culture method. The resulting cultures were purified using a Protein-A affinity column, and then purified proteins were subjected to SDS-PAGE and size-exclusion HPLC (SE-HPLC) to identify purity of the proteins.

As shown in FIGS. 1A-1C, it was identified that all respective proteins purified by the SE-HPLC method have purity of 93% or higher. In addition, as a result of SDS-PAGE analysis, it was identified that proteins having sizes of about 150 kDa and about 75 kDa are detected, respectively, in the non-reducing and reducing conditions (FIG. TA, Lanes 1 to 6). From this, it was found that the Fc-bound FcεRIαECD forms a dimer. In addition, no impurities such as a truncated form were observed in the SDS-PAGE results. In particular, even after the process of thawing/freezing (FIG. TA, Lanes 7 to 8), it was identified that all proteins have purity of 93% or higher, and has no impurities. From this, it was found that production of truncated protein forms is decreased relative to the FcεRIαECD-Fc1 to which the wild type IgD hinge had been applied.

Here, Gel-IEF was performed under the following test conditions to identify a degree of sialic acid content in the proteins following introduction of the sialic acid transferase. From this, it was identified that a content of acidic proteins is increased due to increased sialic acid content.

TABLE 2

| Test conditions | |
| --- | --- |
| Gel | pH3-10 IEF gel 1.0 mm |
| Sample buffer | IEF sample buffer (2×) |
| Loading condition | 100 V 1 hr, 200 V 1 hr, 500 V 2 hr |

In order to identify reproducibility of purification yield, the FcεRIαECD-Fc2ST cell line was batch-cultured in a 1 L flask at a 250 ml scale and purified using a Protein-A affinity column. Subsequently, the culture supernatant and the purified product were subjected to running on a 4% to 15% TGX™ Precast Protein gel (TGX: Tris-Glycine eXtended, Bio-Rad Laboratories, Inc.) for 30 minutes at a condition of Tris-Glycine SDS (TGS) buffer and 200 V, and then subjected to SDS PAGE analysis. As a result, it was identified that not only proteins with very high purity (98% or higher) are purified even by only the first step purification but also proteins are expressed with very high purity even in the culture supernatant. This indicates that process development steps can be simplified in developing the FcεRIαECD-Fc protein, which had been expressed in the cell line in question, into a medical product, and as a result, it is highly likely for the development cost of the medical product to be remarkably decreased.

Example 3. Identification of Binding Ability of FcεRIα ECD Fusion Protein to IgE A binding ability to IgE was comparatively measured for the four proteins, i) FcεRIαECD-Fc2, ii) FcεRIαECD-Fc2ST, iii) FcεRIαECD-Fc3, and iv) FcεRIαECD-Fc3ST which had been purified through the method of Example 2 above, and the commercially available anti-IgE antibody, omalizumab (trade name: XOLAIR®). Specifically, the binding ability to IgE was measured by coating IgE on the channel of the Protein GLC sensor chip (Bio-Rad Laboratories, Inc., Cat #176-5011), and causing omalizumab or each FcεR1αECD-Fc protein at various concentrations to flow at a rate of 30 μl per minute.

The experiments were conducted by identifying zero base using 25 mM NaOH as a regeneration buffer, and then repeating the above steps. Thereafter, a binding curve was identified using a protein binding analyzer (PROTEON™ XPR36 protein interaction array system, Bio-Rad Laboratories, Inc., USA). The results are shown in Table 3, and FIGS. 3 and 4.

TABLE 3

| Samples items Drug type | | FcεRIa ECD-Fc Fc fusion protein | | Omalizumab Anti-IgE Ab | Remarks |
| --- | --- | --- | --- | --- | --- |
| Binding affinity | ka (association rate) | Fc2 | $2.14 \times 10^5$ | $4.05 \times 10^5$ | 1.9-fold weaker than omalizumab |
| | | Fc2ST | $2.64 \times 10^5$ | | 1.5-fold weaker than omalizumab |
| | | Fc3 | $1.98 \times 10^5$ | | 2.0-fold weaker than omalizumab |
| | | Fc3ST | $2.40 \times 10^5$ | | 1.7-fold weaker than omalizumab |
| | kd (dissociation rate) | Fc2 | $8.29 \times 10^{-5}$ | $6.02 \times 10^{-3}$ | 73-fold better than omalizumab |
| | | Fc2ST | $5.69 \times 10^{-5}$ | | 106-fold better than omalizumab |
| | | Fc3 | $1.33 \times 10^{-4}$ | | 45-fold better than omalizumab |
| | | Fc3ST | $1.49 \times 10^{-4}$ | | 40-fold better than omalizumab |
| | KD (kd/ka) | Fc2 | $3.88 \times 10^{-10}$ | $1.49 \times 10^{-8}$ | 38-fold better than omalizumab |
| | | Fc2ST | $2.16 \times 10^{-10}$ | | 69-fold better than omalizumab |
| | | Fc3 | $6.72 \times 10^{-10}$ | | 22-fold better than omalizumab |
| | | Fc3ST | $6.21 \times 10^{-10}$ | | 24-fold better than omalizumab |

As shown in Table 3, the association rate (ka) value of the polypeptide dimer according to an embodiment of the present invention was measured to be 1.5- to 2.0-fold lower than that of omalizumab. That is, it was found that a binding ability thereof to substances other than IgE is 1.5- to 2.0-fold lower than that of omalizumab. In addition, the dissociation rate (kd) value of the polypeptide dimer according to an embodiment of the present invention was measured to be 40- to 106-fold higher than that of omalizumab. In addition, as shown in FIGS. 3 and 4, it was able to identify that omalizumab loses its binding to IgE in a case where a certain period of time has passed after the binding, whereas once the polypeptide dimer of the FcεRIαECD fusion protein of the present invention binds to IgE, the polypeptide dimer is not separated from IgE.

That is, it can be seen that the polypeptide dimer of the present invention is not easily separated from IgE, and has a much better ability to maintain its bound state than omalizumab. As a result, it can be seen that the polypeptide dimer according to an embodiment of the present invention has an equilibrium dissociation constant (KD<kd/ka>) value which is 22- to 69-fold higher than omalizumab. From this, it was identified that the FcεRIαECD fusion protein of the present invention has a remarkably increased binding ability to IgE as compared with omalizumab. In particular, it was identified that the FcεRIαECD-Fc2 (FcεRIαECD-Fc2ST) to which sialic acid is added exhibits the highest IgE-binding capacity which is 69-fold higher than omalizumab.

Example 4. Identification of Binding Ability of FcεRIα ECD Fusion Protein to IgG Receptor A degree of binding of $IgE_{TRAP}$ and omalizumab to IgG receptors was identified using the OCTET® RED384 system (FORTEBIO™, Sartorius AG, CA, USA). FcγRI, FcγRIIA, FcγRIIB, FcγRIIIA, and FcγRIIIB recombinant proteins (R & D Systems Inc., 5 μg/ml) were immobilized in 300 mM acetate buffer (pH 5) on the activated AR2G biosensor. As a running buffer, PBS containing 0.1% Tween-20 and 1% bovine serum was used. All experiments were carried out at 30° C. with a sample plate shaker at a rate of 1,000 rpm. The results are shown in FIGS. 5A to 5E, and binding abilities of omalizumab and $IgE_{TRAP}$ to the IgG receptors are quantified and shown in FIG. 6.

Example 5. Identification of Activity of FcεRIα ECD Fusion Protein Through Beta-Hexosaminidase Assay in Mouse Bone Marrow-Derived Mast Cells Beta-hexosaminidase assay was performed for in vitro activity analysis of the FcεRIαECD fusion protein of the present invention. Specifically, the FcεRIαECD-Fc2 protein according to an embodiment of the present invention was mixed, at each concentration, with mouse IgE (1 ug/mL), and incubated at room temperature (20° C.) for 30 minutes to prepare samples. Mouse bone marrow-derived mast cells in culture for mast cell activation were washed with Hank's balanced salt solution (HBSS) buffer to remove the medium, and the number of cells was measured. Then, an adjustment was made so that $5\times10^5$ cells were injected into 40 μL of HBSS buffer.

Then, 50 uL of the sample solution prepared through the pre-incubation was added to the activated mast cells. Then, the resultant was incubated in a 5% $CO_2$ incubator at 37° C. for 30 minutes. Subsequently, after the addition of each 10 μL of DNP (2,4-dinitrophenol, 100 ng/mL), which is a foreign antigen, incubation was performed again at 37° C. for 30 minutes in 5% $CO_2$, and then 30 μL of the supernatant was separated. 30 uL of the separated supernatant and 30 uL of the substrate (4-nitrophenyl N-acetyl-β-D-glucosaminide, 5.84 mM) were mixed well, and then incubated at 37° C. for 20 minutes in 5% $CO_2$. Then, 140 μL of 0.1 M sodium carbonate buffer (pH 10) as a stop solution was added to terminate the reaction. Thereafter, absorbance at 405 nm was measured to identify a secretion amount of β-hexosaminidase secreted by the foreign antigen in the activated mast cells. The results are shown in FIG. 7.

As shown in FIG. 7, the polypeptide dimer of an embodiment of the present invention exhibited a mast cell inhibition ratio of about 49.4% in a case of having half (0.5 ug/mL) the concentration of mouse IgE, and exhibited a mast cell inhibition ratio of about 99.4% in a case of having the same concentration (1 ug/mL) of mouse IgE. That is, it can be seen that IgE-induced activity of bone marrow-derived mast cells is greatly suppressed by the FcεRIα-ECD polypeptide dimer of the present invention.

Example 6. Comparison of Activity of FcεRIα ECD Fusion Protein and Anti-Human IgE Antibody Using β-Hexosaminidase Assay in Human FcΣRI-Expressing Bone Marrow-Derived Mast Cells β-Hexosaminidase assay was conducted to identify superiority of the FcεRIα ECD fusion protein relative to XOLAIR® through in vitro activity analysis. The respective drugs, FcεRIαECD-Fc2ST ($IgE_{TRAP}$) and XOLAIR®, were prepared at each concentration, and then mixed with human IgE (1 ug/mL). Then, incubation was performed at room temperature for 30 minutes. During pre-incubation of the drug, a human FcεRI gene was introduced, and mast cells derived from and differentiated from mouse bone marrow, in which the mouse FcεRI gene had been removed, were prepared. The prepared mast cells were washed with HBSS buffer, and then $5\times10^5$ cells were injected into 60 μL of HBSS buffer. 20 μL of the pre-incubated sample was added to the prepared mast cells, and then incubated in a 5% $CO_2$ incubator at 37° C. for 30 minutes.

Subsequently, after 20 μL of anti-human IgE antibody (BioLegend, Inc., Cat No. 325502, 0.5 ug/mL) was added, and then the resultant was incubated again in 5% $CO_2$ incubator at 37° C. for 30 minutes. Subsequently, after centrifugation at 1,500 rpm at 4° C., 30 uL of the supernatant was separated. 30 uL of the separated supernatant and 30 uL of the substrate (4-nitrophenyl N-acetyl-μ-glucosaminide, 5.84 mM) were mixed well, and then incubated in a 5% $CO_2$ incubator at 37° C. for 25 minutes. Then, 140 uL of 0.1 M sodium carbonate buffer (pH 10) was added to terminate the reaction.

Subsequently, absorbance at 405 nm was measured to compare relative amounts of secreted β-hexosaminidase, and a mass cell-inhibitory effect depending on each drug concentration was identified. The results are shown in FIG. 8. As shown in FIG. 8, $IC_{50}$ of the FcεRIα ECD fusion protein was measured to be approximately 11.16 ng/mL, and $IC_{50}$ of the XOLAIR® protein was measured to be approximately 649.8 ng/mL. Therefore, it was identified that the FcεRIα ECD fusion protein has a 58-fold higher inhibitory ability on mast cell activity than XOLAIR®.

Example 7. In Vivo Assay of FcεRIα ECD Fusion Protein (Food Allergy Model)

50 μg of ovalbumin (OVA) and 1 mg of alum were intraperitoneally administered to Balb/c mice (Orientbio Inc.) two times at a 14-day interval to induce sensitization. Thereafter, 50 mg of OVA was orally administered five times in total on days 28, 30, 32, 34, and 36, to induce food allergy in intestines.

After the OVA was orally administered two times, that is, on day 31, the mice were divided into three groups, each containing 7 mice. The three divided groups were as follows: The first group receiving the FcεRIαECD-Fc2ST fusion protein at a high concentration (200 ug), the second group receiving the FcεRIαECD-Fc2ST fusion protein at a low concentration (20 ug), and the third group receiving nothing. While orally administering the OVA, it was identified whether diarrhea occurs due to food allergy induction. The mice were sacrificed on day 37, and the number of mast cells in the small intestine, the IgE concentration in blood, and the concentration of enzyme (mast cell protease-1 (MCPT-1)) with mast cell degranulation in blood were analyzed for the mice belonging to each group.

As shown in FIG. 9, it was identified that the mice belonging to the group receiving the FcεRIαECD-Fc2ST, which is a polypeptide dimer, at a high concentration exhibits an effect of alleviating food allergy in a concentration-dependent manner, as compared with the mice belonging to the group receiving nothing.

[Sequence List Text]

```
                                                             SEQ ID NO: 1
VPQKPKVSLN PPWNRIFKGE NVTLTCNGNN FFEVSSTKWF HNGSLSEETN SSLNIVNAKF

EDSGEYKCQH QQVNESEPVY LEVFSDWLLL QASAEVVMEG QPLFLRCHGW RNWDVYKVIY

YKDGEALKYW YENHNISITN ATVEDSGTYY CTGKVWQLDY ESEPLNITVI KAPREKYWLQ

SEQ ID NO: 2
SHTQPLGVFL FPPKPKDTLM ISRTPEVTCV VVDVSQEDPE VQFNWYVDGV EVHNAKTKPR

EEQFNSTYRV VSVLTVLHQD WLNGKEYKCK VSNKGLPSSI EKTISKAKGQ PREPQVYTLP

PSQEEMTKNQ VSLTCLVKGF YPSDIAVEWE SNGQPENNYK TTPPVLDSDG SFFLYSRLTV

DKSRWQEGNV FSCSVMHEAL HNHYTQKSLS LSLGK

SEQ ID NO: 3
RNTGRGGEEK KGSKEKEEQE ERETKTPECP

SEQ ID NO: 4
AQPQAEGSLA KATTAPATTR NTGRGGEEKK GSKEKEEQEE RETKTPECP

SEQ ID NO: 5
gtgcccaga  agcccaaggt  gagcctgaac  cctccctgga  acagaatctt  caagggcgag aacgtgaccc tgacctgcaa cggcaacaac ttcttcgagg tgagcagcac caagtggttc cacaatggca gcctgagcga ggagaccaac agctccctga acatcgtgaa cgccaagttc gaggacagcg gcgagtacaa gtgccagcac cagcaggtga acgagagcga gcccgtgtac ctggaggtgt tcagcgactg gctgctgctg caggccagcg ccgaggtggt gatggagggc cagcccctgt tcctgagatg ccacggctgg agaaactggg acgtgtacaa ggtgatctac tacaaggatg gcgaggccct gaagtactgg tacgagaacc acaacatctc catcaccaac gccaccgtgg aggacagcgg cacctactac tgcacaggca aggtgtggca gctggactac gagagcgagc ccctgaacat caccgtgatc aaggctccca gagagaagta ctggctgcag SEQ ID NO: 6
tgcgtggtcg tggatgtgag ccaggaagat cccgaagtgc agttcaactg gtacgtggat ggcgtggaag tgcacaacgc caagaccaag cccagagaag agcagttcaa ctccacctac agagtggtga gcgtgctgac cgtgctgcac caggactggc tgaacggcaa ggagtacaag tgcaaggtgt ccaacaaagg cctgcccagc tccatcgaga agaccatcag caaagccaaa ggccagccca gagaacccca ggtgtacacc ctgcctccca gccaggaaga gatgaccaag aaccaggtgt ccctgacctg cctggtgaaa ggcttctacc ccagcgacat cgccgtggag tgggaaagca acggccagcc cgagaacaat tacaagacaa cccctcccgt gctggatagc gatggcagct tctttctgta cagcagactg accgtggaca gagcagatg gcaggaaggc aacgtgttca gctgcagcgt gatgcacgaa gccctgcaca ccactacac ccagaagagc ctgtccctga gcctgggcaa g
```

```
                                                      SEQ ID NO: 7
aggaacaccg gcagaggagg cgaggaaaag aaaggaagca aggagaagga ggagcaggag gaaagagaaa ccaagacccc cgagtgcccc agccacaccc agccctggg cgtgttcctg ttcccccca agcccaagga caccctgatg atcagcagaa ccccgaggt gacc SEQ ID NO: 8
gcccagcccc aggccgaggg cagcctggct aaggccacca cagctcccgc caccaccagg aacaccggca gaggaggcga ggaaaagaaa ggaagcaagg agaaggagga gcaggaggaa agagaaacca agacccccga gtgccccagc cacacccagc ccctgggcgt gttcctgttc cccccaagc ccaaggacac cctgatgatc agcagaaccc cgaggtgac c

SEQ ID NO: 9
MDAMLRGLCC VLLLCGAVFV SPSHA

SEQ ID NO: 10
atggacgcca tgctgagagg cctgtgctgt gtgctgctgc tgtgcggcgc cgtgttcgtg tcccctagcc acgcc

SEQ ID NO: 11
MDAMLRGLCC VLLLCGAVFV SPSHAVPQKP KVSLNPPWNR IFKGENVTLT CNGNNFFEVS

STKWFHNGSL SEETNSSLNI VNAKFEDSGE YKCQHQQVNE SEPVYLEVFS DWLLLQASAE

VVMEGQPLFL RCHGWRNWDV YKVIYYKDGE ALKYWYENHN ISITNATVED SGTYYCTGKV

WQLDYESEPL NITVIKAPRE KYWLQRNTGR GGEEKKGSKE KEEQEERETK TPECPSHTQP

LGVFLFPPKP KDTLMISRTP EVTCVVVDVS QEDPEVQFNW YVDGVEVHNA KTKPREEQFN

STYRVVSVLT VLHQDWLNGK EYKCKVSNKG LPSSIEKTIS KAKGQPREPQ VYTLPPSQEE

MTKNQVSLTC LVKGFYP SDIAVEWESNGQP ENNYKTTPPV LDSDGSFFLY SRLTVDKSRW

QEGNVFSCSV MHEALHNHYT QKSLSLSLGK

SEQ ID NO: 12
atggacgcca tgctgagagg cctgtgctgt gtgctgctgc tgtgcggcgc cgtgttcgtg tcccctagcc acgccgtgcc ccagaagccc aaggtgagct gaaccctcc ctggaacaga atcttcaagg gcgagaacgt gaccctgacc tgcaacggca caacttctt cgaggtgagc agcaccaagt ggttccacaa tggcagcctg agcgaggaga ccaacagctc cctgaacatc gtgaacgcca agttcgagga cagcggcgag tacaagtgcc agcaccagca ggtgaacgag agcgagcccg tgtacctgga ggtgttcagc gactggctgc tgctgcaggc cagcgccgag gtggtgatgg agggccagcc cctgttcctg agatgccacg gctggagaaa ctgggacgtg tacaaggtga tctactacaa ggatggcgag gccctgaagt actggtacga gaaccacaac atctccatca ccaacgccac cgtggaggac agcggcacct actactgcac aggcaaggtg tggcagctgg actacgagag cgagcccctg aacatcaccg tgatcaaggc tcccagagag aagtactggc tgcagaggaa caccggcaga ggaggcgagg aaaagaaagg aagcaaggag aaggaggagc aggaggaaag agaaaccaag accccgagt gccccagcca cacccagccc ctgggcgtgt tcctgttccc cccaagccc aaggacaccc tgatgatcag cagaaccccc gaggtgacct gcgtggtcgt ggatgtgagc caggaagatc ccgaagtgca gttcaactgg tacgtggatg gcgtggaagt gcacaacgcc aagaccaagc cagagaaga gcagttcaac tccacctaca gagtggtgag cgtgctgacc gtgctgcacc aggactggct gaacggcaag gagtacaagt gcaaggtgtc caacaaaggc ctgcccagct ccatcgagaa gaccatcagc aaagccaaag gccagcccag agaacccag gtgtacaccc tgcctcccag ccaggaagag atgaccaaga accaggtgtc cctgacctgc ctggtgaaag gcttctaccc cagcgacatc
```

-continued gccgtggagt gggaaagcaa cggccagccc gagaacaatt acaagacaac ccctcccgtg ctggatagcg atggcagctt ctttctgtac agcagactga ccgtggacaa gagcagatgg caggaaggca acgtgttcag ctgcagcgtg atgcacgaag ccctgcacaa ccactacacc cagaagagcc tgtccctgag cctgggcaag

SEQ ID NO: 13
MDAMLRGLCC VLLLCGAVFV SPSHAVPQKP KVSLNPPWNR IFKGENVTLT CNGNNFFEVS

STKWFHNGSL SEETNSSLNI VNAKFEDSGE YKCQHQQVNE SEPVYLEVFS DWLLLQASAE

VVMEGQPLFL RCHGWRNWDV YKVIYYKDGE ALKYWYENHN ISITNATVED SGTYYCTGKV

WQLDYESEPL NITVIKAPRE KYWLQAQPQA EGSLAKATTA PATTRNTGRG GEEKKGSKEK

EEQEERETKT PECPSHTQPL GVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPPSQEEM TKNQVSLTCL VKGFYPSDIA VEWESNGQPE NNYKTTPPVL

DSDGSFFLYS RLTVDKSRWQ EGNVFSCSVM HEALHNHYTQ KSLSLSLGK

SEQ ID NO: 14
atggacgcca tgctgagagg cctgtgctgt gtgctgctgc tgtgcggcgc cgtgttcgtg tcccctagcc acgccgtgcc ccagaagccc aaggtgagcc tgaaccctcc ctggaacaga atcttcaagg gcgagaacgt gaccctgacc tgcaacggca caacttcttt cgaggtgagc agcaccaagt ggttccacaa tggcagcctg agcgaggaga ccaacagctc cctgaacatc gtgaacgcca agttcgagga cagcggcgag tacaagtgcc agcaccagca ggtgaacgag agcgagcccg tgtacctgga ggtgttcagc gactggctgc tgctgcaggc cagcgccgag gtggtgatgg agggccagcc cctgttcctg agatgccacg gctggagaaa ctgggacgtg tacaaggtga tctactacaa ggatggcgag gccctgaagt actggtacga gaaccacaac atctccatca ccaacgccac cgtggaggac agcggcacct actactgcac aggcaaggtg tggcagctgg actacgagag cgagcccctg aacatcaccg tgatcaaggc tcccagagag aagtactggc tgcaggccca gccccaggcc gagggcagcc tggctaaggc caccacagct cccgccacca ccaggaacac cggcagagga ggcgaggaaa agaaaggaag caaggagaag gaggagcagg aggaaagaga aaccaagacc cccgagtgcc cagccacac ccagcccctg ggcgtgttcc tgttcccccc caagcccaag gacaccctga tgatcagcag aaccccgag gtgacctgcg tggtcgtgga tgtgagccag gaagatcccg aagtgcagtt caactggtac gtggatggcg tggaagtgca caacgccaag accaagccca gaagagca gttcaactcc acctacagag tggtgagcgt gctgaccgtg ctgcaccagg actggctgaa cggcaaggag tacaagtgca aggtgtccaa caagggcctg cccagctcca tcgagaagac catcagcaaa gccaaggcc agcccagaga ccccaggtg tacaccctgc ctcccagcca ggaagagatg accaagaacc aggtgtccct gacctgcctg gtgaaaggct tctacccag cgacatcgcc gtggagtggg aaagcaacgg ccagcccgag aacaattaca gacaacccc tcccgtgctg gatagcgatg gcagcttctt tctgtacagc agactgaccg tggacaagag cagatggcag gaaggcaacg tgttcagctg cagcgtgatg cacgaagccc tgcacaacca ctacacccag aagagcctgt ccctgagcct gggcaag

SEQ ID NO: 15
MIHTNLKKKF SCCVLVFLLF AVICVWKEKK KGSYYDSFKL QTKEFQVLKS LGKLAMGSDS

QSVSSSSTQD PHRGRQTLGS LRGLAKAKPE ASFQVWNKDS SSKNLIPRLQ KIWKNYLSMN

KYKVSYKGPG PGIKFSAEAL RCHLRDHVNV SMVEVTDFPF NTSEWEGYLP KESIRTKAGP

-continued

```
WGRCAVVSSA GSLKSSQLGR EIDDHDAVLR FNGAPTANFQ QDVGTKTTIR LMNSQLVTTE

KRFLKDSLYN EGILIVWDPS VYHSDIPKWY QNPDYNFFNN YKTYRKLHPN QPFYILKPQM

PWELWDILQE ISPEEIQPNP PSSGMLGIII MMTLCDQVDI YEFLPSKRKT DVCYYYQKFF

DSACTMGAYH PLLYEKNLVK HLNQGTDEDI YLLGKATLPG FRTIHC
```

SEQ ID NO: 16
```
atgatccaca ccaacctgaa gaagaagttc agctgctgcg tgctggtgtt cctgctgttc gccgtgatct gcgtgtggaa ggagaagaag aaaggcagct actacgacag cttcaagctg cagaccaagg agttccaggt gctgaagagc ctgggcaagc tggccatggg cagcgacagc cagagcgtgt ccagctcctc cacccaggat ccccacagag cagacagac cctgggcagc ctgagaggcc tggccaaggc caagcccgag ccagcttcc aggtgtggaa caaggacagc agcagcaaga acctgatccc cagactgcag aagatctgga gaactacct gagcatgaac aagtacaagg tgagctacaa aggacccgga cccggcatca gttcagcgc cgaggccctg aggtgccacc tgagagacca cgtgaacgtg agcatggtgg aagtgaccga cttcccttc aacaccagcg agtgggaagg ctacctgccc aaggagagca tcaggaccaa ggctggcccc tggggcagat gcgccgtggt gagcagcgct ggcagcctga agagctccca gctgggcaga gagatcgacg accacgatgc cgtgctgagg ttcaatggcg ctcccaccgc caacttccag caggacgtgg gcaccaagac cacaatccgg ctgatgaaca gccagctggt gacaaccgag aagcggttcc tgaaggacag cctgtacaac gagggcatcc tgatcgtgtg ggatcccagc gtgtaccaca gcgacatccc caagtggtac cagaatcccg actacaactt cttcaacaac tacaagacct atagaaagct gcaccccaac cagcccttct acatcctgaa gcccagatg ccctgggagc tgtgggacat cctgcaggag atcagccctg aagagatcca gcccaaccct ccctccagcg gcatgctggg cattatcatc atgatgaccc tgtgcgacca ggtggacatc tacgagttcc tgcccagcaa gagaaagacc gacgtgtgct actactatca gaagttcttc gacagcgcct gcaccatggg cgcctaccac cccctgctgt acgagaagaa cctggtgaag cacctgaacc agggcaccga cgaggacatc tacctgctgg gcaaagccac cctgcccggc ttcagaacca tccactgc
```

SEQ ID NO: 17
RNTGRGGEEK KXXKEKEEQE ERETKTPECP

SEQ ID NO: 18
AQPQAEGSLA KATTAPATTR NTGRGGEEKK XXKEKEEQEE RETKTPECP

SEQ ID NO: 19
RNTGRGGEEK KKEKEKEEQE ERETKTPECP

SEQ ID NO: 20
```
VPQKPKVSLN PPWNRIFKGE NVTLTCNGNN FFEVSSTKWF HNGSLSEETN SSLNIVNAKF

EDSGEYKCQH QQVNESEPVY LEVFSDWLLL QASAEVVMEG QPLFLRCHGW RNWDVYKVIY

YKDGEALKYW YENHNISITN ATVEDSGTYY CTGKVWQLDY ESEPLNITVI KAPREKYWLQ

RNTGRGGEEK KKEKEKEEQE ERETKTPECP SHTQPLGVFL FPPKPKDTLM ISRTPEVTCV

VVDVSQEDPE VQFNWYVDGV EVHNAKTKPR EEQFNSTYRV VSVLTVLHQD WLNGKEYKCK

VSNKGLPSSI EKTISKAKGQ PREPQVYTLP PSQEEMTKNQ VSLTCLVKGF YPSDIAVEWE

SNGQPENNYK TTPPVLDSDG SFFLYSRLTV DKSRWQEGNV FSCSVMHEAL HNHYTQKSLS

LSLGK
```

SEQ ID NO: 21
```
VPQKPKVSLN PPWNRIFKGE NVTLTCNGNN FFEVSSTKWF HNGSLSEETN SSLNIVNAKF

EDSGEYKCQH QQVNESEPVY LEVFSDWLLL QASAEVVMEG QPLFLRCHGW RNWDVYKVIY
```

-continued

```
YKDGEALKYW YENHNISITN ATVEDSGTYY CTGKVWQLDY ESEPLNITVI KAPREKYWLQ

RNTGRGGEEK KGSKEKEEQE ERETKTPECP SHTQPLGVFL FPPKPKDTLM ISRTPEVTCV

VVDVSQEDPE VQFNWYVDGV EVHNAKTKPR EEQFNSTYRV VSVLTVLHQD WLNGKEYKCK

VSNKGLPSSI EKTISKAKGQ PREPQVYTLP PSQEEMTKNQ VSLTCLVKGF YPSDIAVEWE

SNGQPENNYK TTPPVLDSDG SFFLYSRLTV DKSRWQEGNV FSCSVMHEAL HNHYTQKSLS

LSLGK

SEQ ID NO: 22
VPQKPKVSLN PPWNRIFKGE NVTLTCNGNN FFEVSSTKWF HNGSLSEETN SSLNIVNAKF

EDSGEYKCQH QQVNESEPVY LEVFSDWLLL QASAEVVMEG QPLFLRCHGW RNWDVYKVIY

YKDGEALKYW YENHNISITN ATVEDSGTYY CTGKVWQLDY ESEPLNITVI KAPREKYWLQ

AQPQAEGSLA KATTAPATTR NTGRGGEEKK GSKEKEEQEE RETKTPECPS HTQPLGVFLF

PPKPKDTLMI SRTPEVTCVV VDVSQEDPEV QFNWYVDGVE VHNAKTKPRE EQFNSTYRVV

SVLTVLHQDW LNGKEYKCKV SNKGLPSSIE KTISKAKGQP REPQVYTLPP SQEEMTKNQV

SLTCLVKGFY PSDIAVEWES NGQPENNYKT TPPVLDSDGS FFLYSRLTVD KSRWQEGNVF

SCSVMHEALH NHYTQKSLSL SLGK
```

The invention claimed is:

1. A polypeptide dimer, comprising:
two monomers, each of which comprises an extracellular domain of an alpha subunit of an IgE Fc receptor (FcεRIα-ECD) consisting of the amino acid sequence of SEQ ID NO: 1, wherein each of the two monomers comprises a modified Fc region consisting of the amino acid sequence of SEQ ID NO: 2, wherein the N-terminus of the modified Fc region is linked via a hinge to the C-terminus of the FcεRIα-ECD to have a structure of N'-FcεRIα-ECD-hinge-modified Fc region-C', and wherein the hinge comprises the amino acid sequence of SEQ ID NO: 3.

2. A pharmaceutical composition comprising the polypeptide dimer according to claim 1, as an active ingredient.

3. A food composition comprising the polypeptide dimer according to claim 1.

4. A polynucleotide that encodes a monomer of the polypeptide dimer according to claim 1, which wherein the monomer contains an extracellular domain of an alpha subunit of an IgE Fc receptor (FcεRIα-ECD) consisting of the amino acid sequence of SEQ ID NO: 1; wherein the monomer comprises a modified Fc region consisting of the amino acid sequence of SEQ ID NO: 2; wherein the N-terminus of the modified Fc region is linked via a hinge to the C-terminus of the FcεRIα-ECD to have a structure of N'-FcεRIα-ECD-hinge-modified Fc region-C'; and wherein the hinge comprises the amino acid sequence of SEQ ID NO: 3.

5. An expression vector, comprising the polynucleotide according to claim 4.

6. An isolated host cell comprising the expression vector according to claim 5.

7. A method for producing the polypeptide dimer of claim 1, comprising: a step of culturing a cell, into which (a) a polynucleotide encoding a monomer of the polypeptide dimer and (b) a sialic acid transferase gene is introduced, under a condition for expression of the polynucleotide, wherein the monomer contains an extracellular domain of an alpha subunit of an IgE Fc receptor (FcεRIα-ECD) consisting of the amino acid sequence of SEQ ID NO: 1; wherein the monomer comprises a modified Fc region consisting of the amino acid sequence of SEQ ID NO: 2; wherein the N-terminus of the modified Fc region is linked via a hinge to the C-terminus of the FcεRIα-ECD to have a structure of N'-FcεRIα-ECD-hinge-modified Fc region-C'; and wherein the hinge comprises the amino acid sequence of SEQ ID NO: 3; and a step of recovering the polypeptide dimer.

8. The polypeptide dimer obtained by the method of claim 7.

9. A pharmaceutical composition comprising, as an active ingredient, the polypeptide dimer according to claim 8.

10. A food composition comprising, as an active ingredient, the polypeptide dimer according to claim 8.

11. A method for treating a food allergy in a subject in need thereof, comprising: a step of administering to the subject an effective amount of the polypeptide dimer according to claim 1.

12. A method for treating a food allergy in a subject in need thereof, comprising: a step of administering to the subject an effective amount of the polypeptide dimer according to claim 8.

* * * * *